United States Patent
Honjo et al.

(10) Patent No.: US 11,568,535 B2
(45) Date of Patent: Jan. 31, 2023

(54) MEDICAL IMAGE PROCESSING APPARATUS, ULTRASOUND DIAGNOSIS APPARATUS, AND TRAINED MODEL GENERATING METHOD

(71) Applicant: CANON MEDICAL SYSTEMS CORPORATION, Otawara (JP)

(72) Inventors: Yasunori Honjo, Utsunomiya (JP); Keita Yonemori, Utsunomiya (JP); Masaki Watanabe, Utsunomiya (JP); Yuko Takada, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 420 days.

(21) Appl. No.: 16/856,153

(22) Filed: Apr. 23, 2020

(65) Prior Publication Data
US 2020/0342593 A1    Oct. 29, 2020

(30) Foreign Application Priority Data
Apr. 26, 2019    (JP) .............................. JP2019-085933

(51) Int. Cl.
*G06T 7/00*    (2017.01)
*A61B 8/08*    (2006.01)
*A61B 8/14*    (2006.01)

(52) U.S. Cl.
CPC .......... *G06T 7/0012* (2013.01); *A61B 8/0883* (2013.01); *A61B 8/14* (2013.01); *A61B 8/488* (2013.01); *A61B 8/5207* (2013.01); *A61B 8/5246* (2013.01); *G06T 2207/10132* (2013.01); *G06T 2207/20081* (2013.01); *G06T 2207/30048* (2013.01)

(58) Field of Classification Search
CPC ......... G06T 7/0012; G06T 2207/10132; G06T 2207/20081; G06T 2207/30048; A61B 8/0883; A61B 8/14; A61B 8/488; A61B 8/5207; A61B 8/5246; A61B 8/483; A61B 8/5276; G06V 10/774; G06N 3/08; G01S 7/52038; G01S 15/8915; G06K 9/6262
USPC ....................................................... 382/228
See application file for complete search history.

(56) References Cited

U.S. PATENT DOCUMENTS

| 2004/0158149 | A1 | 8/2004 | McLaughlin et al. |
| 2014/0009808 | A1 | 1/2014 | Wang et al. |
| 2015/0324957 | A1 | 11/2015 | Honjo et al. |
| 2019/0336101 | A1* | 11/2019 | Chiang .................... A61B 1/00 |

(Continued)

OTHER PUBLICATIONS

Office Action dated Nov. 1, 2022 in corresponding Japanese Patent Application No. 2019-085933.

(Continued)

*Primary Examiner* — Ali Bayat
(74) *Attorney, Agent, or Firm* — Oblon, McClelland, Maier & Neustadt, L.L.P.

(57) ABSTRACT

A medical image processing apparatus according to an embodiment includes processing circuitry configured to generate an output data set apparently expressing a second data set obtained by transmitting and receiving an ultrasound wave, for each scanning line, as many times as a second number that is larger than a first number, by inputting a first data set to a trained model that generates the output data set on a basis of the first data set obtained by transmitting and receiving an ultrasound wave as many times as the first number for each scanning line.

23 Claims, 10 Drawing Sheets

(56) References Cited

U.S. PATENT DOCUMENTS

| | | | |
|---|---|---|---|
| 2020/0107818 A1* | 4/2020 | Keshet | A61B 8/5246 |
| 2020/0178933 A1* | 6/2020 | Imai | A61B 8/5223 |
| 2020/0245967 A1* | 8/2020 | Venugopal | A61B 5/02042 |
| 2020/0253585 A1* | 8/2020 | Neben | A61B 8/0841 |
| 2020/0286228 A1* | 9/2020 | Guenther | G06T 7/0012 |
| 2020/0320694 A1* | 10/2020 | Howell | A61B 8/483 |
| 2020/0390419 A1* | 12/2020 | Neben | A61B 8/08 |
| 2021/0015456 A1* | 1/2021 | Chiang | A61B 8/0883 |

OTHER PUBLICATIONS

Gasse, Maxime et al., High-Quality Plane Wave Compounding Using Convolutional Neural Networks, IEEE Transactions On Ultrasonics, Ferroelectrics, and Frequency Control, IEEE, vol. 64, No. 10, pp. 1637-1639, Oct. 6, 2017.

* cited by examiner

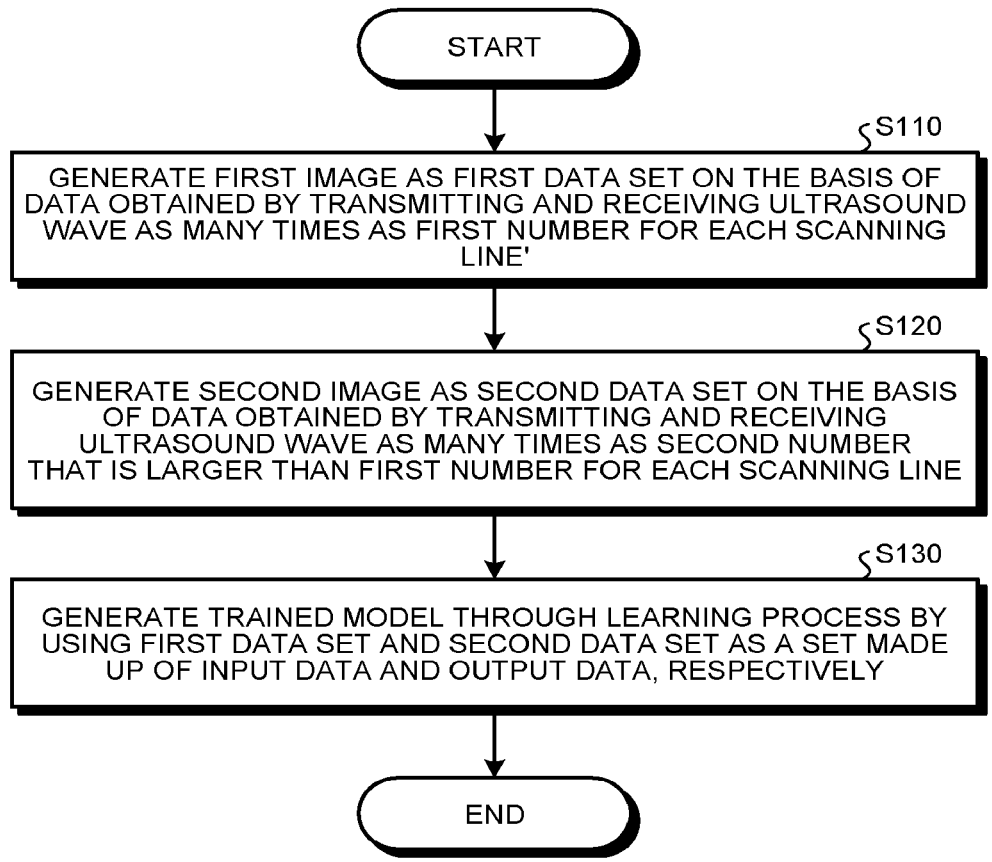
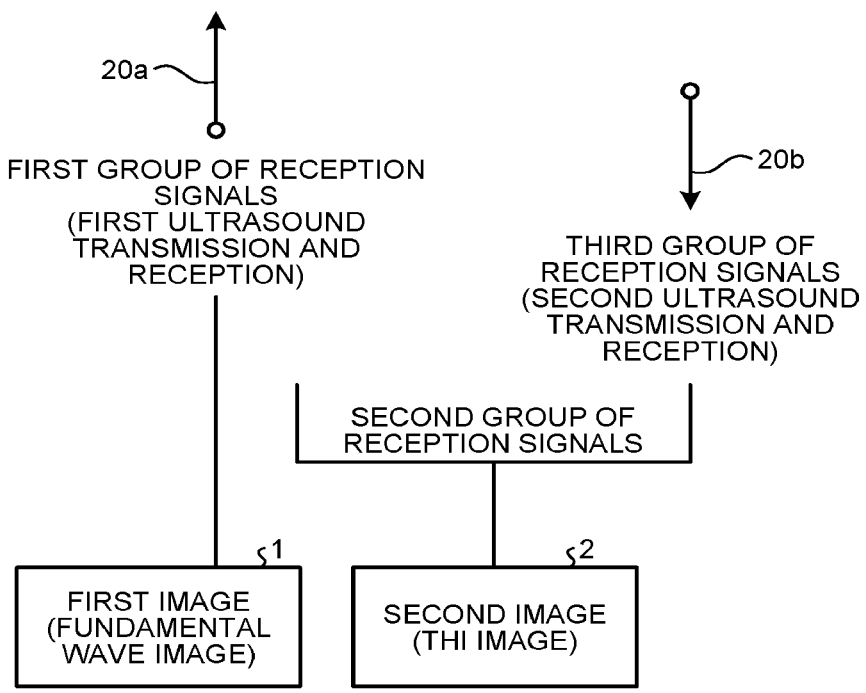

FIRST GROUP OF RECEPTION SIGNALS (FIRST ULTRASOUND TRANSMISSION AND RECEPTION)

THIRD GROUP OF RECEPTION SIGNALS (SECOND ULTRASOUND TRANSMISSION AND RECEPTION)

SECOND GROUP OF RECEPTION SIGNALS

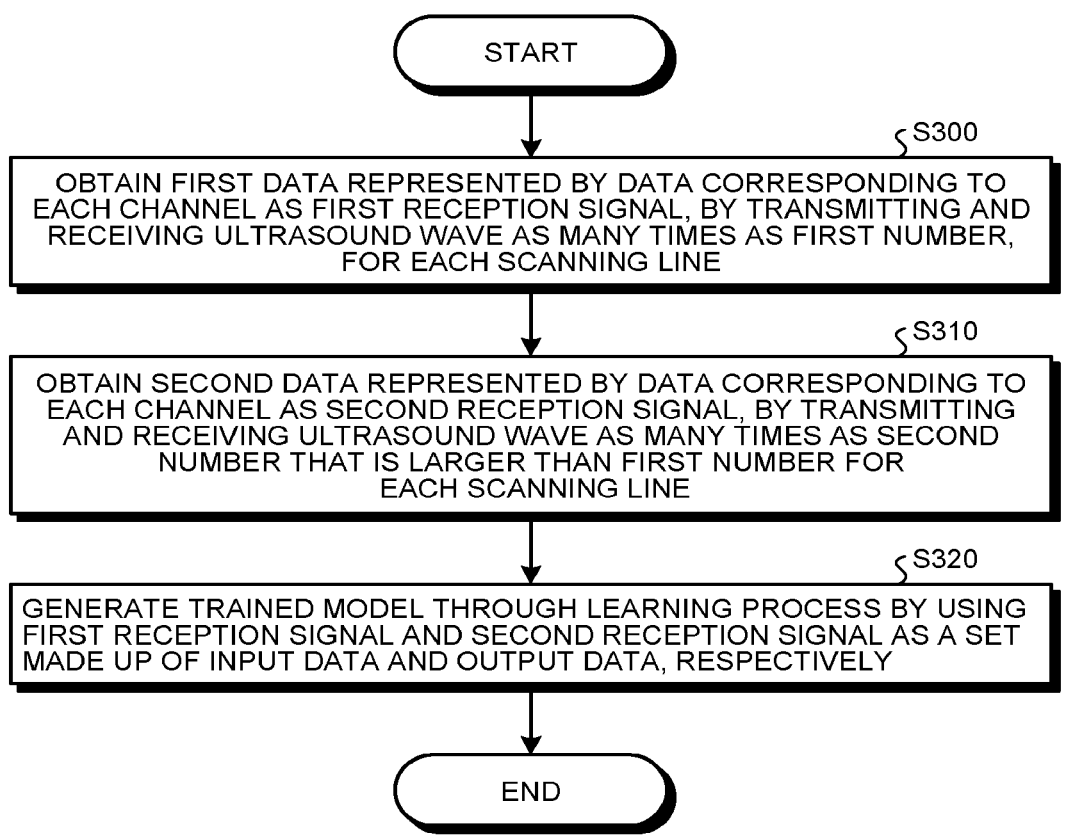

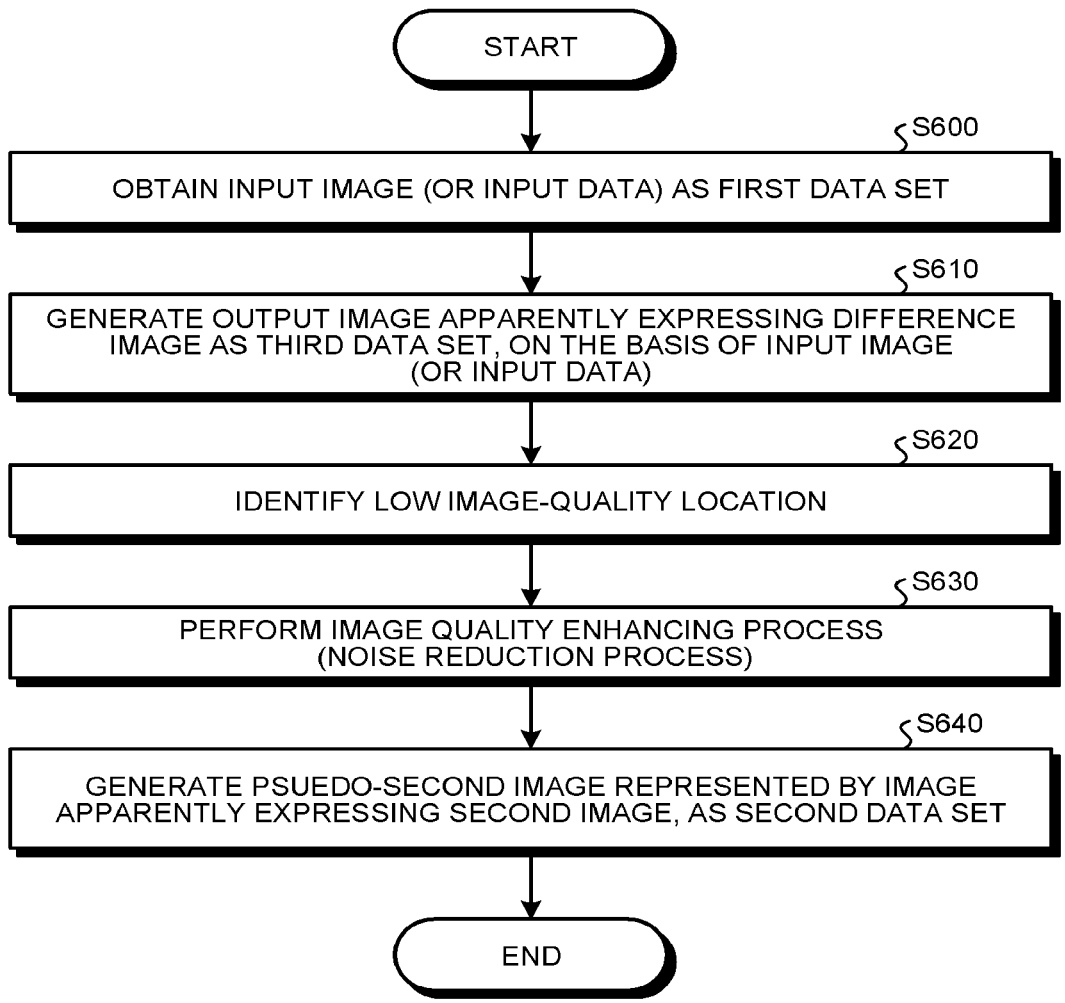

MEDICAL IMAGE PROCESSING APPARATUS, ULTRASOUND DIAGNOSIS APPARATUS, AND TRAINED MODEL GENERATING METHOD

CROSS-REFERENCE TO RELATED APPLICATIONS

This application is based upon and claims the benefit of priority from Japanese Patent Application No. 2019-085933, filed on Apr. 26, 2019; the entire contents of which are incorporated herein by reference.

FIELD

Embodiments described herein relate generally to a medical image processing apparatus, an ultrasound diagnosis apparatus, and a trained model.

BACKGROUND

With ultrasound diagnosis apparatuses, a technique is known by which high-quality images can be obtained by transmitting and receiving an ultrasound wave multiple times for each scanning line while varying a transmission parameter such as the phase, the deflection angle, the frequency, or the like and combining together obtained reception signals related to mutually the same scanning line. Examples of this technique include Tissue Harmonic Imaging (THI) methods and Differential Tissue Harmonic Imaging (Diff-THI) methods.

When using one of these techniques by which high-harmonic signals are extracted by transmitting and receiving the ultrasound wave multiple times for each scanning line, obtaining an image in one frame requires a longer period of time, compared to when an ultrasound wave is transmitted and received once, for each scanning line. As a result, the framerate is lower. In other words, in the above example, the image quality and the framerate are in a trade-off relationship.

In addition, regarding a site (e.g., the heart) that moves at a high speed, when an ultrasound wave is transmitted and received multiple times for each scanning line, image quality is degraded because the site moves before an upcoming ultrasound wave is transmitted and received. For this reason, it may be difficult in some situations to image this kind of site by transmitting and receiving an ultrasound wave multiple times for each scanning line.

BRIEF DESCRIPTION OF THE DRAWINGS

FIG. 2 is a flowchart for explaining a flow in a learning process performed by a medical image processing apparatus according to a first embodiment;

FIG. 3 is a drawing for explaining processes performed by the medical image processing apparatus according to the first embodiment;

FIG. 9 is a flowchart for explaining a flow in a learning process performed by a medical image processing apparatus according to a second embodiment;

FIG. 12 is a flowchart for explaining a flow in another process of implementing the trained model performed by the medical image processing apparatus according to the fourth embodiment.

DETAILED DESCRIPTION

Figure 1:
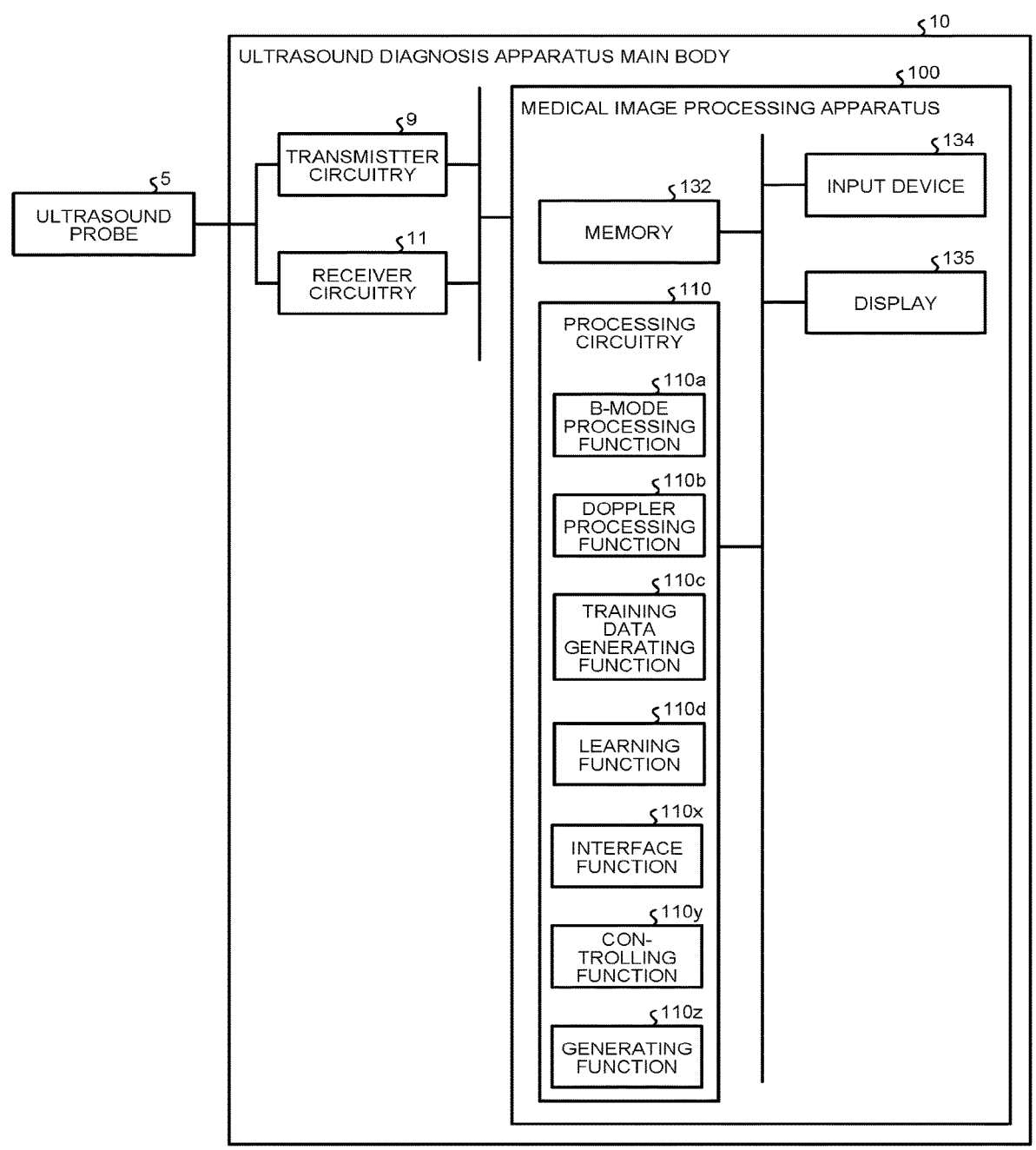
FIG. 1 is a diagram illustrating a medical image processing apparatus and an ultrasound diagnosis apparatus according to an embodiment.

A medical image processing apparatus according to an embodiment includes processing circuitry configured: to generate an output data set apparently expressing a second data set obtained by transmitting and receiving an ultrasound wave as many times as a second number larger than a first number for each scanning line, by inputting a first data set to a trained model that generates the output data set on a basis of the first data set obtained by transmitting and receiving an ultrasound wave as many times as the first number, for each scanning line.

Embodiments of the present disclosure will be explained below, with reference to the accompanying drawings. Some of the constituent elements that are the same as one another will be referred to by using the same reference characters, and duplicate explanations thereof will be omitted.

First Embodiment

Configurations of a medical image processing apparatus and an ultrasound diagnosis apparatus according to a first embodiment will be explained. FIG. 1 is a block diagram illustrating exemplary configurations of the medical image processing apparatus and the ultrasound diagnosis apparatus according to the first embodiment. As illustrated in FIG. 1, the ultrasound diagnosis apparatus according to the first embodiment includes an ultrasound probe 5 and an ultrasound diagnosis apparatus main body 10. The ultrasound diagnosis apparatus main body 10 includes transmitter circuitry 9, a reception 11, and a medical image processing apparatus 100.

The ultrasound probe 5 includes a plurality of piezoelectric transducer elements. Each of the plurality of piezoelectric transducer elements is configured to generate an ultrasound wave on the basis of a drive signal supplied thereto from a transmitter circuitry 9 included in the ultrasound diagnosis apparatus main body 10 (explained later). Further, each of the plurality of piezoelectric transducer elements included in the ultrasound probe 5 is configured to receive reflected waves from an examined subject (hereinafter "patient") P and to convert the received reflected waves into electric signals (reflected-wave signals). Further, the ultrasound probe 5 includes a matching layer provided for the piezoelectric transducer elements, as well as a backing member or the like that prevents the ultrasound waves from propagating rearward from the piezoelectric transducer elements. In this situation, the ultrasound probe 5 is detachably connected to the ultrasound diagnosis apparatus main body 10.

When an ultrasound wave is transmitted from the ultrasound probe 5 to the patient P, the transmitted ultrasound wave is repeatedly reflected on a surface of discontinuity of acoustic impedances at a tissue in the body of the patient P and is received as a reflected wave by the plurality of elements included in the ultrasound probe 5 before being converted into a reflected-wave signal. The amplitude of the reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members for the ultrasound wave transmission direction.

The present embodiments are applicable to situations where the ultrasound probe 5 is a one-dimensional (1D) array probe configured to two-dimensionally scan the patient P and to situations where the ultrasound probe 5 is a mechanical four-dimensional (4D) probe or a two-dimensional (2D) array probe configured to three-dimensionally scan the patient P.

The ultrasound diagnosis apparatus main body 10 is an apparatus configured to generate ultrasound image data on the basis of the reflected-wave signals received from the ultrasound probe 5. The ultrasound diagnosis apparatus main body 10 illustrated in FIG. 1 is an apparatus capable of generating two-dimensional ultrasound image data on the basis of two-dimensional reflected-wave signals and capable of generating three-dimensional ultrasound image data on the basis of three-dimensional reflected-wave signals. The embodiments, however, are also applicable to situations where the ultrasound diagnosis apparatus main body 10 is an apparatus dedicated for two-dimensional data.

The ultrasound diagnosis apparatus main body 10 includes, as illustrated in FIG. 1, the transmission circuit 9, the reception circuit 11, and the medical image processing apparatus 100.

The transmission circuit 9 and the reception circuit 11 are configured to control the ultrasound transmission and reception performed by the ultrasound probe 5, on the basis of instructions from processing circuitry 110 including a controlling function 110y (explained later). The transmission circuitry 9 includes a pulse generator, a transmission delay unit, a pulser, and the like and is configured to supply the drive signal to the ultrasound probe 5. The pulse generator is configured to repeatedly generate a rate pulse for forming a transmission ultrasound wave at a predetermined Pulse Repetition Frequency [PRF]. Further, the transmission delay unit is configured to apply a delay time period that is required to converge the ultrasound waves generated by the ultrasound probe 5 into the form of a beam and to determine transmission directionality and that corresponds to each of the piezoelectric transducer elements, to each of the rate pulses generated by the pulse generator. Also, the pulser is configured to apply the drive signal (a drive pulse) to the ultrasound probe 5 with timing based on the rate pulses.

In other words, by varying the delay time periods applied to the rate pulses, the transmission delay unit is configured to arbitrarily adjust the transmission directions of the ultrasound waves transmitted from the surfaces of the piezoelectric transducer elements. Further, by varying the delay time periods applied to the rate pulses, the transmission delay unit is configured to control the positions of converge points (transmission focuses) in the depth direction of the ultrasound transmissions.

In this situation, the transmitter circuitry 9 has a function that is able to instantly change the transmission frequency, the transmission drive voltage, and the like, for the purpose of executing a predetermined scan sequence according to instructions from the processing circuitry 110 (explained later). In particular, the function to change the transmission drive voltage is realized by using a linear-amplifier-type transmission circuit of which the value can be instantly switched or by using a mechanism configured to electrically switch between a plurality of power source units.

Further, the receiver circuitry 11 includes an amplifier circuitry, an Analog/Digital (A/D) converter, a reception delay circuitry, an adder, quadrature detecting circuitry, and the like and is configured to generate reception signals (reflected-wave data) by performing various types of processes on the reflected-wave signals received from the ultrasound probe 5. The amplifier circuitry is configured to amplify the reflected-wave signals for each of the channels and to perform a gain correcting process. The A/D converter is configured to perform an A/D conversion on the gain-corrected reflected-wave signals. The reception delay circuitry is configured to apply reception delay periods required to determine reception directionality, to the digital data. The adder is configured to perform an adding process to the reflected-wave signals to which the reception delay time periods have been applied by the reception delay circuitry. As a result of the adding process performed by the adder, reflected components of the reflected-wave signals that are from the direction corresponding to the reception directionality are emphasized. Further, the quadrature detecting circuitry is configured to convert output signals of the adder into an In-phase signal (an I signal) and a Quadrature-phase signal (a Q signal) that are in a baseband. Further, the quadrature detecting circuitry is configured to transmit the I signal and the Q signal (hereinafter, "IQ signals") to the processing circuitry 110, as the reception signals (the reflected-wave data). In this situation, the quadrature detection circuitry may convert the output signal of the adder into a Radio Frequency (RF) signal before transmitting the signal to the processing circuitry 110. The IQ signals and the RF signals serve as reception signals having phase information.

When a two-dimensional region inside the patient P is to be scanned, the transmitter circuitry 9 causes an ultrasound beam for scanning the two-dimensional region to be transmitted from the ultrasound probe 5. After that, the receiver circuitry 11 generates two-dimensional reception signals from two-dimensional reflected-wave signals received from the ultrasound probe 5. In contrast, when a three-dimensional region inside the patient P is to be scanned, the transmitter circuitry 9 causes an ultrasound beam for scanning the three-dimensional region to be transmitted from the ultrasound probe 5. After that, the receiver circuitry 11 generates three-dimensional reception signals from three-dimensional reflected-wave signals received from the ultrasound probe 5. Further, the receiver circuitry 11 generates reception signals on the basis of the reflected-wave signals and transmits the generated reception signals to the processing circuitry 110.

The transmitter circuitry 9 is configured to cause the ultrasound probe 5 to transmit an ultrasound beam from a predetermined transmission position (a transmission scanning line). The receiver circuitry 11 is configured to receive, from the ultrasound probe 5, the signal derived from the reflected wave of the ultrasound beam transmitted by the transmitter circuitry 9, in a predetermined reception position (a reception scanning line). When a parallel simultaneous reception is not performed, the transmission scanning line and the reception scanning line are the same scanning line. In contrast, when a parallel simultaneous reception is performed, after the transmitter circuitry 9 causes the ultrasound probe 5 to transmit the ultrasound beam at a time from one transmission scanning line, the receiver circuitry 11 simultaneously receives signals of the reflected waves derived from the ultrasound beam which the transmitter circuitry 9 caused the ultrasound probe 5 to transmit, in a plurality of predetermined reception positions (reception scanning lines) as a plurality of reception beams via the ultrasound probe 5.

The medical image processing apparatus 100 is connected to the transmitter circuitry 9 and to the receiver circuitry 11 and is configured to process signals received from the receiver circuitry 11 and to control the transmitter circuitry 9, as well as to generate a trained model, to implement the trained model, and to perform various types of image processing processes. The medical image processing apparatus 100 includes the processing circuitry 110, a memory 132, an input device 134, and a display 135. The processing circuitry 110 includes a B-mode processing function 110a, a Doppler processing function 110b, a training data generating function 110c, a learning function 110d, an interface function 110x, the controlling function 110y, and a generating function 110z.

In the present embodiments, processing functions executed by the B-mode processing function 110a, the Doppler processing function 110b, the training data generating function 110c, the learning function 110d, the interface function 110x, the controlling function 110y, and the generating function 110z as well as the trained model are stored in the memory 132 in the form of computer-executable programs. The processing circuitry 110 is a processor configured to realize the functions corresponding to the programs by reading and executing the programs from the memory 132. In other words, the processing circuitry 110 that has read the programs have the functions illustrated within the processing circuitry 110 in FIG. 1. Further, the processing circuitry 110 that has read the program corresponding to the trained model is capable of performing processes according to the trained model. In this situation, although FIG. 1 illustrates the example in which the functions of the processing circuitry 110 are realized by a single processing circuitry, it is also acceptable to structure the processing circuitry 110 by combining together a plurality of independent processors, so that the functions are realized as a result of the processors executing the programs. In other words, each of the abovementioned functions may be configured as a program, so that a single processing circuitry executes each of the programs. Further, it is also acceptable to realize two or more of the functions included in the processing circuitry 110 by using one processing circuitry. Alternatively, any specific function may be installed in a dedicated independent program executing circuitry.

In FIG. 1, the processing circuitry 110, the B-mode processing function 110a, the Doppler processing function 110b, the training data generating function 110c, the learning function 110d, the interface function 110x, the controlling function 110y, and the generating function 110z are examples of a processing unit, a B-mode processing unit, a Doppler processing unit, a generating unit, a learning unit, a receiving unit, a controlling unit, and a generating unit, respectively. The generating function 110z further has functions as a combining unit (explained later).

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 132.

Further, instead of saving the programs in the memory 132, it is also acceptable to directly incorporate the programs into the circuits of the processors. In that situation, the processors realize the functions by reading and executing the programs incorporated in the circuits thereof. Accordingly, for example, instead of saving the trained model in the memory 132, it is also acceptable to directly incorporate the program related to the trained model in the circuit of a processor. Further, the transmitter circuitry 9, the receiver circuitry 11, and the like built in the ultrasound diagnosis apparatus main body 10 may be configured by using hardware such as one or more integrated circuits or the like or by using programs structured as modules in the manner of software.

The processing circuitry 110 is a processing unit configured to perform various types of signal processing processes on the reception signals received from the receiver circuitry 11. The processing circuitry 110 includes the B-mode processing function 110a, the Doppler processing function 110b, the training data generating function 110c, the learning function 110d, the interface function 110x, the controlling function 110y, and the generating function 110z.

By employing the B-mode processing function 110a, the processing circuitry 110 is configured to generate data (B-mode data) in which signal intensities are expressed with degrees of brightness, by receiving data from the receiver circuitry 11 and performing thereon a logarithmic amplification process, an envelope detecting process, a logarithmic compressing process, or the like.

Further, by employing the Doppler processing function 110b, the processing circuitry 110 is configured to generate data (Doppler data) obtained by extracting, for a large number of points, moving member information such as velocity, dispersion, power, and the like based on the Doppler effect, by performing a frequency analysis on the reception signals (the reflected-wave data) received from the receiver circuitry 11 to acquire velocity information.

The B-mode processing function 110a and the Doppler processing function 110b illustrated in FIG. 1 are capable of processing both two-dimensional reflected-wave data and three-dimensional reflected-wave data.

By employing the interface function 110x, the processing circuitry 110 is configured to obtain data used for the image generation by the generating function 110z, images, and the like, from the receiver circuitry 11 and the memory 132.

By employing the training data generating function 110c, the processing circuitry 110 is configured to generate training data for learning processes, on the basis of the data and the images obtained by the interface function 110x Details of processes performed by the training data generating function 110c and the learning function 110d will be explained later.

By employing the learning function 110d, the processing circuitry 110 is configured to generate the trained model by performing the learning processes by using the training data generated by the training data generating function 110c.

By employing the controlling function 110y, the processing circuitry 110 is configured to control the entirety of processes performed by the ultrasound diagnosis apparatus. More specifically, by employing the controlling function 110y, the processing circuitry 110 is configured to control processes performed by the transmitter circuitry 9, the receiver circuitry 11, and the processing circuitry 110, on the basis of various types of setting requests input by an operator via the input device 134 and various types of control programs and various types of data read from the memory 132. Further, by employing the controlling function 110y, the processing circuitry 110 is configured to exercise control so that the display 135 displays any of the display-purpose ultrasound image data stored in the memory 132.

By employing the generating function 110z, the processing circuitry 110 is configured to generate the ultrasound image data from the data generated by the B-mode processing function 110a and the Doppler processing function 110b. By employing the generating function 110z, the processing circuitry 110 is configured to generate two-dimensional B-mode image data in which intensities of the reflected waves are expressed as brightness levels, from two-dimensional B-mode data generated by the B-mode processing function 110a. Further, by employing the generating function 110z, the processing circuitry 110 is configured to generate two-dimensional Doppler image data expressing moving member information, from two-dimensional Doppler data generated by the Doppler processing function 110b. The two-dimensional Doppler image data is velocity image data, dispersion image data, power image data, or image data combining together any of these types of image data.

Further, by employing the generating function 110z, the processing circuitry 110 is configured to convert (by performing a scan convert process) a scanning line signal sequence from an ultrasound scan into a scanning line signal sequence in a video format used by, for example, television and to generate display-purpose ultrasound image data. Further, as various types of image processing processes besides the scan convert process, the processing circuitry 110 performs, by employing the generating function 110z, an image processing process (a smoothing process) to re-generate an average brightness value image, an image processing process (an edge enhancement process) that uses a differential filter inside an image or the like, for example, by using a plurality of image frames resulting from the scan convert process. Also, by employing the generating function 110z, the processing circuitry 110 is configured to perform various types of rendering processes on volume data, to generate two-dimensional image data used for displaying the volume data on the display 135.

Further, by employing the generating function 110z, the processing circuitry 110 is configured to generate images on the basis of results of processes performed by employing the training data generating function 110c and the learning function 110d. Further, by employing the generating function 110z, the processing circuitry 110 is configured to apply the trained model generated by the learning function 110d to input images and to generate images on the basis of results of the application of the trained model.

The memory 132 is configured by using a semiconductor memory element such as a Random Access Memory (RAM) or a flash memory, or a hard disk, an optical disk, or the like. The memory 132 is a memory configured to store therein data such as the display-purpose image data, training-purpose image data, and the like generated by the processing circuitry 110. Further, the memory 132 is also capable of storing therein any of the data generated by the B-mode processing function 110a and the Doppler processing function 110h. After a diagnosis process, for example, the operator is able to invoke any of the B-mode data and the Doppler data stored in the memory 132. The invoked data can serve as the display-purpose ultrasound image data after being routed through the processing circuitry 110. Further, the memory 132 is also capable of storing therein the reception signals (the reflected-wave data) output by the receiver circuitry 11.

In addition, the memory 132 is configured to store therein, as necessary, a control program for performing ultrasound transmissions and receptions, image processing processes, and display processes, as well as diagnosis information (e.g., patients' IDs and observations of medical doctors) and various types of data such as diagnosis protocols, various types of body marks, and the like.

The input device 134 is configured to receive various types of instructions and inputs of information from the operator. For example, the input device 134 is a pointing device such as a mouse or a trackball, a selecting device such as a mode changing switch, and/or an input device such as a keyboard.

Under control of the controlling function 110y and the like, the display 135 is configured to display a Graphical User Interface (GUI) used for receiving inputs of image taking conditions and to display images and the like generated by the generating function 110z or the like. The display 135 is, for example, a display such as a liquid crystal display monitor. The display 135 is an example of a display unit. The display 135 includes a mouse, a keyboard, a button, a panel switch, a touch command screen, a foot switch, a trackball, a joystick, and/or the like.

Next, a background of embodiments will briefly be explained.

With ultrasound diagnosis apparatuses, a technique is known by which high-quality images can be obtained by transmitting and receiving an ultrasound wave multiple times for each scanning line while varying a transmission parameter such as the phase, the deflection angle, the frequency, or the like and combining together obtained reception signals related to mutually the same scanning line. Examples in which the varied parameter is the phase include Tissue Harmonic Imaging (THI) methods and Differential Tissue Harmonic Imaging (Diff-THI) methods.

When using one of these techniques by which an ultrasound wave is transmitted and received multiple times for each scanning line, obtaining an image in one frame requires a longer period of time (which lowers the framerate), compared to when an ultrasound wave is transmitted and received once for each scanning line. In other words, in the above example, the image quality and the framerate are in a trade-off relationship.

In addition, regarding a site (e.g., the heart) that moves at a high speed, when an ultrasound wave is transmitted and received multiple times for each scanning line, image quality is degraded because the site moves before an upcoming ultrasound wave is transmitted and received. Accordingly, for this kind of site, it may be difficult in some situations to transmit and receive an ultrasound wave multiple times for each scanning line.

In view of the background described above, in the medical image processing apparatus 100 according to an embodiment, the processing circuitry 110 is configured, by employing the learning function 110d, to generate a trained model by performing a learning process, by using a first image or signal obtained by transmitting and receiving an ultrasound wave as many times as a first number, for each scanning line and a second image or signal obtained by transmitting and receiving an ultrasound wave as many times as a second number that is larger than the first number, for each scanning line, as an input image or signal and as an output image or signal, respectively. As a result, it is possible to obtain an image corresponding to an image obtained by transmitting an ultrasound wave as many times as the second number that is larger than the first number for each scanning line, on the basis of the first image or signal obtained by transmitting an ultrasound wave as many times as the first number, for each scanning line.

This configuration will be explained, with reference to FIGS. 2 to 8. The present example will be explained by using image data as the relevant input/output data; however, possible embodiments are not necessarily limited to using image data, and it is possible to use a group of RF signal data or a group of IQ data obtained before structuring images.

To begin with, a procedure for generating the trained model performed by the processing circuitry 110 while employing the training data generating function 110c and the learning function 110d will be explained, with reference to FIG. 2. FIG. 2 is a flowchart for explaining a flow in a learning process performed by the medical image processing apparatus according to the first embodiment.

At first, the transmitter circuitry 9 causes the ultrasound probe 5 to transmit an ultrasound wave as many times as the second number that is larger than the first number, while varying a transmission parameter for each scanning line. In this situation, for example, the first number is 1, whereas the second number is 2. Further, the transmission parameter may be, for example, the phase of the transmitted ultrasound wave. In the above example, the transmitter circuitry 9 causes the ultrasound probe 5 to transmit the ultrasound wave twice for each scanning line, while varying the phase of the transmitted ultrasound wave for each scanning line. In this situation, varying the phase of the transmitted ultrasound wave does not necessarily have to be varying the phase of all the frequency components included in the ultrasound wave and may be varying the phase of at least one of the frequency components. Further, varying the phase of the transmitted ultrasound wave does not necessarily have to be directly controlling the phase of the transmitted ultrasound wave and may be varying the phase of the transmitted ultrasound wave as a consequence. In one example, changing the shape (the waveform) of the drive signal applied to the piezoelectric transducer elements can consequently vary the phase of the transmitted ultrasound wave.

Subsequently, the receiver circuitry 11 causes the ultrasound probe 5 to receive reception signals corresponding to the ultrasound waves caused by the transmitter circuitry 9 to be transmitted, as a second group of reception signals including a first group of reception signals. The second group of reception signals is a group of reception signals corresponding to the ultrasound waves successively transmitted and received as many times as the second number, for each scanning line and is a group of reception signals used for generating, for example, a non-linear component image in the process explained later. At the same time, the second group of reception signals which the receiver circuitry 11 caused the ultrasound probe 5 to receive includes the first group of reception signals used for generating, for example, a linear component image in the process explained later.

For example, let us discuss an example in which, as illustrated in FIG. 3, the transmitter circuitry 9 causes ultrasound waves to be transmitted twice for each scanning line, while arranging the phase of the ultrasound wave which the ultrasound probe 5 is caused to transmit for each scanning line, so that the initial phase of the first ultrasound transmission is in a first phase (e.g., 0 degrees) whereas the initial phase of the second ultrasound transmission is a second phase (e.g., 180 degrees) different from the first phase. In the present example, as illustrated in FIG. 3, the receiver circuitry 11 causes the ultrasound probe 5 to receive a first group of reception signals 20a resulting from the first ultrasound transmission and reception corresponding to the ultrasound transmission of which the initial phase is 0 degrees and a third group of reception signals 20b corresponding to the ultrasound transmission of which the initial phase is 180 degrees. In this situation, the first group of reception signals 20a and the third group of reception signals 20b structure a second group of reception signals and are used for generating a second image 2, which is a Tissue Harmonic Imaging (THI) image. Further, the first group of reception signals 20a is used for generating a first image 1, which is a fundamental wave image. In the present example, the fundamental wave image does not necessarily require that the high-harmonic component is 0. In the present embodiment, the fundamental wave image may have a small amount of high-harmonic component mixed therein. In the following sections, an example will be explained in which the ultrasound wave which the transmitter circuitry 9 causes the ultrasound probe 5 to transmit is structured with a single frequency component.

Returning to the description of FIG. 2, at step S110, by employing the training data generating function 110c, the processing circuitry 110 generates the first image 1 represented by a linear component image that is a fundamental wave image, as a first data set represented by a linear component image data set, on the basis of the first group of reception signals 20a serving as a plurality of first scanning line data sets. The first group of reception signals 20a corresponds to data obtained by transmitting and receiving an ultrasound wave as many times as the first number for each scanning line. Accordingly, the first image is an image obtained by transmitting and receiving the ultrasound wave as many times as the first number, for each scanning line.

In the following sections, the term "image data set" denotes any of various types of data sets and is a data set that is related to an image and from which it is possible to structure the image directly or indirectly. Accordingly, the image itself is an example of a data form which the image data set can take and is one of examples of the image data set. However, possible data forms of an image data set are not limited to this example. The data set may be any of various types of data sets; for example, even when data is in a form different from an image at a glance, the data may be used for structuring an image when being appropriately processed.

At step S110, instead of the processing circuitry 110 generating the first image 1 by employing the training data generating function 110c, the processing circuitry 110 may obtain, as the first image 1, a first linear component image or a non-linear component image based on the first group of reception signals 20a, from the memory 132 or an external storage device, by employing the interface function 110x, for example.

Subsequently, at step S120, by employing the training data generating function 110c, the processing circuitry 110 generates the second image 2 represented by a non-linear component image that is a THI image, as a second data set represented by a non-linear component image data set, on the basis of the second group of reception signals which is represented by a plurality of second scanning line data sets and includes the first group of reception signals 20a and which is structured with, for example, the first group of reception signals 20a represented by the plurality of first scanning line data sets and the third group of reception signals 20b being different from the first group of reception signals 20a and being represented by a plurality of third scanning line data sets. The second image 2 is an image obtained by transmitting and receiving an ultrasound wave as many times as the second number that is larger than the first number while varying a transmission parameter for each scanning line. The second image 2 represented by the non-linear component image data set is generated by combining, for each scanning line, the second group of reception signals serving as the plurality of second scanning line data sets. The second image 2 is, for example, represented by an image data set based on at least one selected from among a harmonic component of the second or higher order, a difference tone component, and a sum tone component included in the reception signals structuring the second group of reception signals, for example. In the example in FIG. 3, by employing the training data generating function 110c, the processing circuitry 110 generates the second image 2, by performing weighted addition on the second group of reception signals for each scanning line.

Compared to the first image 1, the second image 2 has a larger amount of data per scanning line and is an image rendering even higher-harmonic components, for example, and thus has higher image quality.

At step S120, instead of the processing circuitry 110 generating the second image 2 as the second data set while employing the training data generating function 110c, the processing circuitry 110 may obtain, as the second image 2, a non-linear component image (which is, when a non-linear component image was obtained at step S110, another non-linear component image different from the obtained non-linear component image) based on the second group of reception signals including the first group of reception signals, from the memory 132 or an external storage device, by employing the interface function 110x, for example.

Subsequently, at step S130, by employing the learning function 110d, the processing circuitry 110 generates a trained model through a learning process by using the first data set and second data as a set made up of input data and output data, respectively. More specifically, by employing the learning function 110d, the processing circuitry 110 generates the trained model by performing the learning process while using the first image 1 and the second image 2 as the set made up of the input data and the output data, respectively, by using a neural network or the like, for example. For instance, by employing the learning function 110d, the processing circuitry 110 generates the trained model through the learning process, by using the first image 1 that is the linear component image represented by the linear component image data set based on the first group of reception signals 20a serving as the plurality of first scanning line data sets as the input; and using the second image 2 that is the non-linear component image represented by the non-linear component image data set based on the second group of reception signals which includes the first group of reception signals 20a and which is represented by the plurality of second scanning line data sets corresponding to the ultrasound waves successively transmitted and received as many times as the second number for each scanning line, as the output. In other words, by employing the learning function 110d, the processing circuitry 110 generates the trained model, by using a linear component image (or a non-linear image) as the input-side training data and using a non-linear image (which is, when a non-linear image is obtained as the input-side training data, another non-linear image different from the obtained non-linear image) as the output-side training data. The trained model is configured, upon receipt of an input of an input image obtained by transmitting and receiving an ultrasound wave as many times as the first number, for each scanning line as the first data set, so as to output an output image apparently expressing a second data set (e.g., an image) obtained by transmitting and receiving an ultrasound image as many times as the second number that is larger than the first number for each scanning line, as the output data set.

Figure 4:
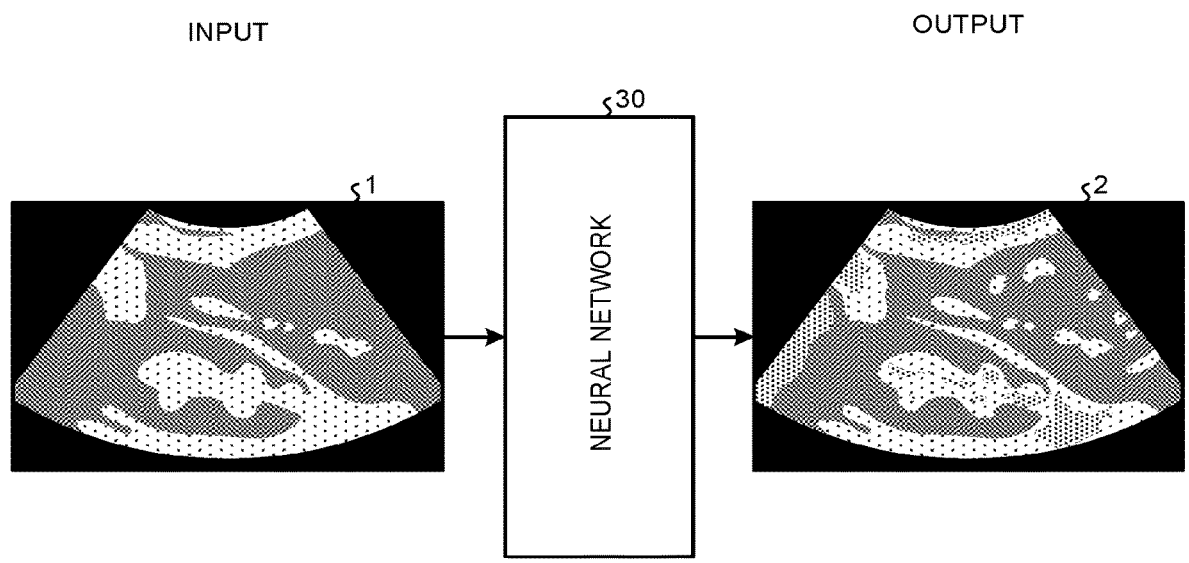
FIG. 4 is another drawing for explaining the processes performed by the medical image processing apparatus according to the first embodiment.

For example, as illustrated in FIG. 4, by employing the learning function 110d, the processing circuitry 110 generates the trained model by performing the learning process, while using the first image 1 serving as an example of the first data set and the second image 2 serving as an example of the second data set, as a set made up of input data and output data for a neural network 30, respectively, and further adjusting weights applied to the neural network 30.

The trained model generated in this manner is a trained model configured to generate the image represented by the output data set apparently expressing the second image 2 represented by the second data set obtained by transmitting and receiving the ultrasound wave as many times as the second number that is larger than the first number, while varying the transmission parameter for each scanning line, on the basis of the first image 1 represented by the first data set obtained by transmitting and receiving the ultrasound wave as many times as the first number, for each scanning line. The trained model generated in this situation is configured to generate the output image having a higher lateral resolution and a higher axial resolution than the input image, as a result of the processing circuitry 110 performing processes on the basis of the input image at the time of implementing the trained model.

In this situation, at the time of generating the trained model at step S130 by employing the learning function 110d, the processing circuitry 110 may perform the learning process by using the entire images or may extract parts of the first image 1 and the second image 2 to perform the learning process only on the extracted parts. When the processing circuitry 110 extracts the parts of the images at the time of generating the trained model at step S130 by employing the learning function 110d, the processing circuitry 110 may generate the parts by random extraction or may extract a specific site by using a pattern matching process or the like.

For example, by employing the learning function 110d, the processing circuitry 110 may generate the trained model by using, for example, an analysis window set in advance. For example, by employing the learning function 110d, from the first image 1 and the second image 2, the processing circuitry 110 uses only the data in the set analysis window as the data to be learned from and will not use the data outside the set analysis window as the data to be learned from. By employing the interface function 110x, for example, the processing circuitry 110 may receive an input related to setting the analysis window from a user.

When the specific site is extracted, the site in the image used at the time of the learning process does not necessarily have to be the same as the site in the image used at the time of implementing the trained model. It is acceptable even when the site in the image used at the time of the learning process is different from the site in the image used at the time of implementing the trained model.

In one example, by employing the learning function 110*d*, the processing circuitry 110 performs the learning process on a site other than such sites that move at a high speed and to which it is therefore difficult to transmit an ultrasound wave multiple times for each scanning line. For example, by employing the learning function 110*d*, the processing circuitry 110 performs the learning process by using images of a site other than the heart as the first image represented by a linear component image and the second image represented by a non-linear component image. After that, when implementing the trained model, the processing circuitry 110 inputs, to the trained model, an image of a site that moves at a high speed and to which it is therefore difficult to transmit an ultrasound wave multiple times for each scanning line, by employing the generating function 110*z*.

For example, at the time of implementing the trained model, the processing circuitry 110 inputs, by employing the generating function 110*z*, an image including the heart to the trained model as an input image. In other words, at the time of implementing the trained model, the input image includes the heart, whereas the first image 1 represented by the linear component image and the second image 2 represented by the non-linear component image used in the learning process do not include the heart. That is to say, the first data set at the time of implementing the trained model is obtained by transmitting and receiving an ultrasound wave to a region including the heart, whereas the first image 1 represented by the linear component image and the second image 2 represented by the non-linear component image used in the learning process do not include the heart. Consequently, by employing the generating function 110*z*, the processing circuitry 110 is able to obtain, as an output image, an image corresponding to an image obtained by transmitting an ultrasound wave multiple times and rendering a site (e.g., a site of the heart) that moves at a high speed and to which it is therefore difficult to transmit an ultrasound wave multiple times for each scanning line.

Alternatively, by employing the learning function 110*d*, the processing circuitry 110 may classify the first image and the second image for each site and perform the learning process separately for each of the mutually-different sites. Further, at step S130, the data format of the output data set does not necessarily have to be images. For example, by employing the learning function 110*d*, the processing circuitry 110 may generate an output data set by inputting the first scanning line data set to a trained model configured to generate an output data set apparently expressing a second scanning line data set obtained by transmitting and receiving an ultrasound wave as many times as the second number that is larger than the first number for a scanning line, on the basis of the first scanning line data set obtained by transmitting and receiving an ultrasound wave as many times as the first number for the scanning line and may further generate an image on the basis of the output data set by employing the generating function 110*z*.

As an example of the learning method at step S130, the processing circuitry 110 may generate the trained model by performing the learning process with a backpropagation method, while employing the learning function 110*d*. Alternatively, the processing circuitry 110 may generate a trained model by performing the learning process through deep learning that uses autoencoding, while employing the learning function 110*d*.

Figure 5:
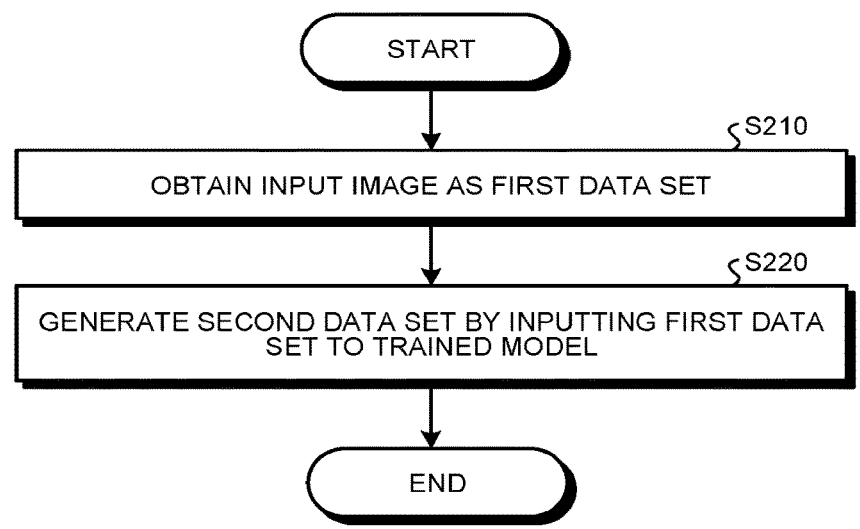
FIG. 5 is a flowchart for explaining a flow in a process of implementing a trained model performed by the medical image processing apparatus according to the first embodiment.

Next, the implementation of the trained model generated by the processing circuitry 110 on the basis of the learning function 110*d* will be explained. FIG. 5 is a flowchart for explaining a flow in the process of implementing the trained model performed by the medical image processing apparatus according to the first embodiment.

To begin with, at step S210, by employing the interface function 110*x*, the processing circuitry 110 obtains an input image acquired by transmitting and receiving an ultrasound wave as many times as the first number for each scanning line, as a first data set. In one example, by employing the interface function 110*x*, the processing circuitry 110 obtains the input image by obtaining a medical image saved in the memory 132. The input image does not necessarily have to be the entirety of the medical image. For example, the input image may be a part of a medical image corresponding to a region of interest. In that situation, it is possible to reduce loads imposed on the processing circuitry 110 and to enhance real-time property related to the generation of the output image, for example.

Subsequently, at step S220, by employing the generating function 110*z*, the processing circuitry 110 generates a second data set by inputting the first data set obtained by the processing circuitry 110 at step S210 by employing the generating function 110*z*, to the trained model generated by the processing circuitry 110 by employing the learning function 110*d*. In one example, by employing the generating function 110*z*, the processing circuitry 110 generates the output image on the basis of the input image obtained at step S210 and the trained model generated by the processing circuitry 110 by employing the learning function 110*d*. In this situation, the output image generated by the processing circuitry 110 by employing the image generating function 110*z* apparently expresses a second image 2 represented by the second data set obtained by transmitting an ultrasound wave as many times as the second number while varying a transmission parameter for each scanning line. For example, the trained model generated by the processing circuitry 110 by employing the learning function 110*d* generates an output image represented by an output data set having a higher lateral resolution and a higher axial resolution than the input image represented by the first data set, on the basis of the input image represented by the first data set obtained at step S210.

Further, by employing the generating function 110*z* serving as a combining unit, the processing circuitry 110 may further obtain a combined image represented by a combined data set, by combining the input image represented by the first data set obtained at step S210 with the output image represented by the output data set generated at step S220, at a ratio corresponding to positions in the axial direction.

In this situation, the reason why the processing circuitry 110 combines, by employing the generating function 110*z*, the input image obtained at step S210 with the output image generated at step S220, at the ratio corresponding to the positions in the axial direction can be explained as follows: For example, a fundamental component image, a second-order harmonic component image, and a third-order harmonic component image have mutually-different magnitudes of attenuation of signal intensities relative to positions in the axial direction (depths). For example, for harmonic component images, as the depth gets deeper, the signal intensities attenuate by a larger degree than for fundamental component images. Accordingly, the processing circuitry 110 is able to obtain an image having a larger S-to-N ratio as a whole, by combining the images together by employing the generating function 110z, while applying a larger weight to the harmonic component image for a location where the depth is shallower and, conversely, applying a larger weight to the fundamental component image for a location where the depth is deeper, for example. Further, for similar reasons, when the processing circuitry 110 has generated, by using the learning function 110d, trained models trained by using non-linear component images having mutually-different frequency bands as output-side training data, a combined image may be obtained by combining together output images (i.e., an output image of a trained model A; and an output image of a trained model B) generated by inputting an input image to the trained models (e.g., the trained model A trained by using the second-order harmonic image as output-side training data; and the trained model B trained by using the third-order harmonic image as training data for output images), at a ratio corresponding to the positions in the axial direction. In this situation, an input image may further be combined with the combined image obtained from this process.

As explained above, by using the medical image processing apparatus according to the first embodiment, it is possible to obtain the image having high image quality.

First Modification Example of First Embodiment

Possible embodiments are not limited to the examples described above.

In the above, the example was explained in which, by employing the learning function 110d, the processing circuitry 110 generates the trained model through the learning process, by using the first image 1 represented by the linear component image based on the first group of reception signals 20a as an input; and using the second image 2 represented by the non-linear component image based on the second group of reception signals as an output; however, possible examples of the first image 1 and the second image 2 in the embodiment are not limited to these examples. The processing circuitry 110 may generate a trained model by using the first image 1 and the second image 2 of various types, by employing the learning function 110d.

Figure 6A:
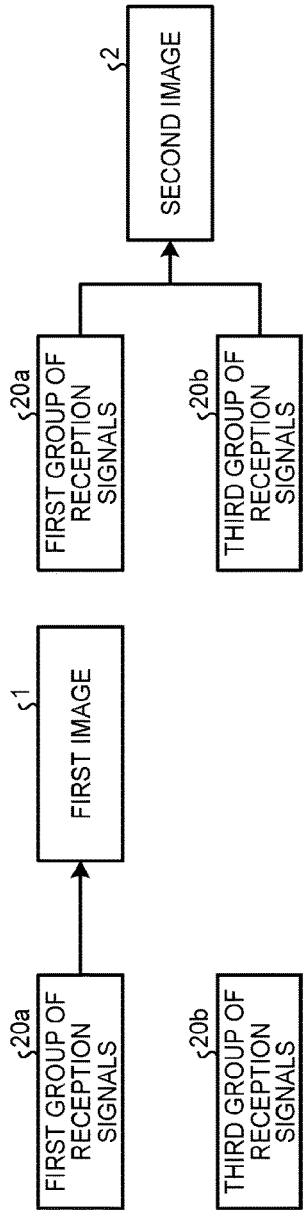
FIGS. 6A, 6B, and 6C present charts for explaining processes performed by a medical image processing apparatus according to a first modification example of the first embodiment.
Figure 6B:
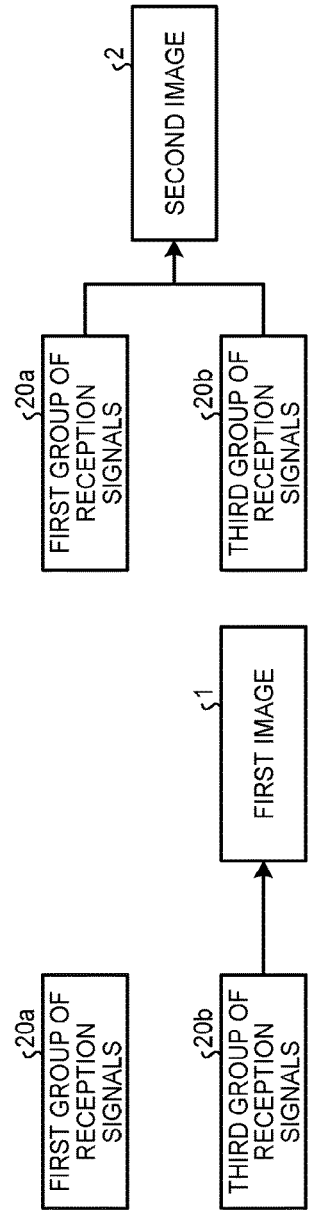
Figure 6C:
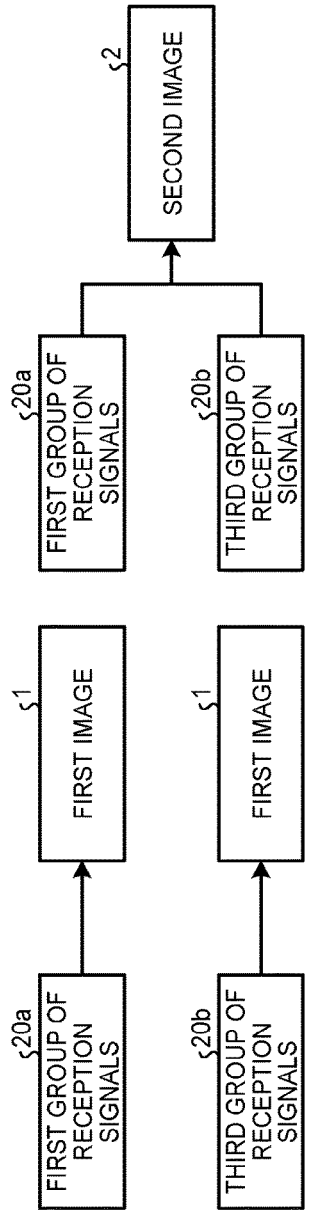

Examples will be explained with reference to FIGS. 6A, 6B, and 6C. FIGS. 6A, 6B, and 6C present charts for explaining processes performed by a medical image processing apparatus according to a first modification example of the first embodiment.

FIG. 6A is a chart corresponding to the generation of the first image 1 and the second image 2 in the example described in the first embodiment. In this situation, by employing the training data generating function 110c, the processing circuitry 110 generates the first image 1 represented by the linear component image that is a fundamental wave image on the basis of the first group of reception signals 20a and generates the second image 2 represented by the non-linear component image that is a THI image on the basis of the second group of reception signals structured with the first group of reception signals 20a and the third group of reception signals 20b or the like. In other words, by employing the learning function 110d, the processing circuitry 110 generates the trained model through the learning process by using, for example, the linear component image based on the first group of reception signals 20a represented by the plurality of first scanning line data sets corresponding to the ultrasound wave transmitted in the first phase as the input and using the non-linear component image based on the second group of reception signals as the output. However, possible embodiments are not limited to this example.

For instance, as illustrated in FIG. 6B, the processing circuitry 110 may generate a first image 1 represented by a linear component image that is a fundamental wave image on the basis of the third group of reception signals 20b that is included in the second group of reception signals but is not included in the first group of reception signals and may generate, by employing the learning function 110d, a trained model by using the generated fundamental wave image 1 as an input image. In other words, by employing the learning function 110d, the processing circuitry 110 may generate the trained model through the learning process, for example, by using, as the input, the linear component image represented by the other linear component image data set based on the third group of reception signals 20b which is represented by the plurality of third scanning line data sets and which is included in the second group of reception signals represented by the plurality of second scanning line data sets but is different from the first group of reception signals 20a represented by the plurality of first scanning line data sets; and using, as the output, the non-linear component image represented by the non-linear image data set. In this situation, the third group of reception signals 20b represented by the plurality of third scanning line data sets is a group of reception signals corresponding to the ultrasound wave transmitted in a second phase different from a first phase, which is the phase of the transmission and reception related to the first group of reception signals 20a.

Further, for example, as illustrated in FIG. 6C, the processing circuitry 110 may, by employing the learning function 110d, perform a learning process by using both the linear component image based on the first group of reception signals 20a and the linear component image based on the third group of reception signals 20b as input images. As a result, it is possible to ensure a larger number of pairs made up of input-side training data and output-side training data and to thus generate a trained model having higher capabilities.

Second Modification Example of First Embodiment

Although FIG. 3 illustrates the example in which the first number is 1, possible embodiments are not limited to the example in which the first number is 1. Further, possible embodiments are not limited to the example in which the first image 1 is a linear component image. In one example, by employing the training data generating function 110c, the processing circuitry 110 may extract a non-linear component while eliminating a fundamental component by applying a frequency filter to a first group of reception signals represented by a plurality of first scanning line data sets, and may further generate a first non-linear component image based on the first group of reception signals represented by the plurality of first scanning line data sets as a first non-linear component image data set serving as a first data set. Further, by employing the training data generating function 110c, the processing circuitry 110 combines, for each scanning line, the second group of reception signals which is represented by the plurality of second scanning line data sets and which includes the first group of reception signals represented by the plurality of first scanning line data sets, so as to generate a second non-linear component image as a second non-linear component image data set serving as a second data set. In one example, the first non-linear component image is a second-order harmonic image, whereas the second non-linear component image is a third-order harmonic image.

Subsequently, by employing the learning function 110d, the processing circuitry 110 may generate a trained model through a learning process, by using the first non-linear component image represented by the first non-linear component image set based on the first group of reception signals represented by the plurality of first scanning line data sets as an input; and using the second non-linear image represented by the second non-linear component image data set based on the second group of reception signals which is represented by the plurality of second scanning line data sets and which includes the first group of reception signals represented by the plurality of first scanning line data sets, as an output.

In this situation, the first non-linear component image and the second non-linear component image are both a non-linear component image. However, the first non-linear component image is based on an image obtained by transmitting and receiving an ultrasound wave as many times as the first number for each scanning line. In contrast, the second non-linear component image is based on an image obtained by transmitting and receiving an ultrasound wave as many times as the second number that is larger than the first number for each scanning line. In other words, in the present example, the plurality of second scanning line data sets correspond to the ultrasound waves successively transmitted and received as many times as the second number, for each scanning line. Accordingly, by employing the learning function 110d, the processing circuitry 110 is able to generate an image having high image quality, by performing the learning process that estimates the image resulting from the larger number of times of transmission on the basis of the image resulting from the smaller number of times of transmission and further generating the image apparently expressing the second non-linear component image having relatively high image quality, on the basis of the first non-linear component image having relatively low image quality.

Similarly to the first embodiment, by employing the learning function 110d, the processing circuitry 110 may perform a learning process by using images of a site other than the heart as a first non-linear component image and a second non-linear component image. Subsequently, at the time of implementing the trained model, the processing circuitry 110 may input an image including (rendering) the heart as an input image to the trained model, by employing the generating function 110z. In that situation, the input image includes (renders) the heart at the time of implementing the trained model, whereas the first non-linear component image and the second non-linear component image used in the learning process do not include (render) the heart. In other words, the first data set used at the time of implementing the trained model is obtained by transmitting and receiving an ultrasound wave to and from a region including (rendering) the heart, i.e., the image data set included in the first data set includes (renders) the heart. In contrast, the first image 1 that is a linear-component image represented by the linear component image and the second image 2 that is a non-linear component image represented by the non-linear component image data set used in the learning process do not include (render) the heart. Accordingly, by employing the generating function 110z, the processing circuitry 110 is able to obtain, as the output image, an image corresponding to an image obtained by transmitting an ultrasound wave multiple times and rendering a site (e.g., a site of the heart) that moves at a high speed and to which it is therefore difficult to transmit an ultrasound wave multiple times for each scanning line.

Third Modification Example of First Embodiment

Further, in the embodiments, the example was explained in which a two-rate transmission is performed, i.e., the process is performed while the ultrasound transmission and reception performed twice is regarded as one block of ultrasound transmission and reception, and also, the ultrasound wave is transmitted and received at a single frequency; however possible embodiments are not limited to this example. Other examples will be explained with reference to FIGS. 7A, 7B, 7C, 8A, 8B, and 8C. FIGS. 7A, 7B, 7C, 8A, 8B, and 8C are drawings for explaining processes performed by a medical image processing apparatus according to a third modification example of the first embodiment.

First, an example of the two-rate transmission will be explained.

Figure 7A:
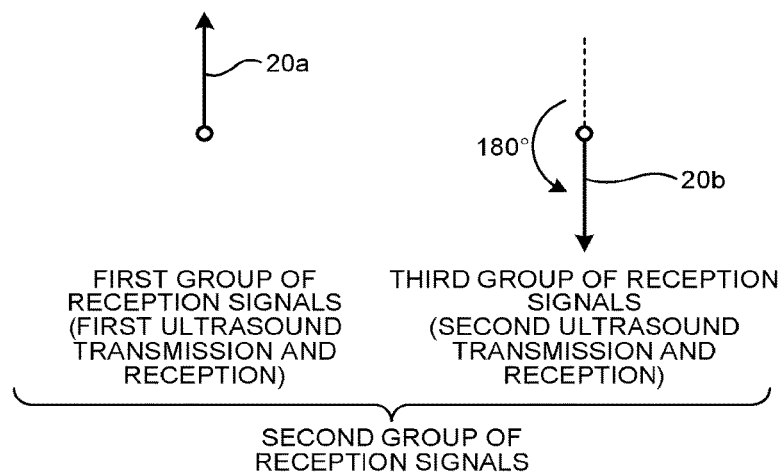
FIGS. 7A, 7B, and 7C present drawings for explaining processes performed by a medical image processing apparatus according to a third modification example of the first embodiment.

As explained in FIG. 7A, the transmitter circuitry 9 causes the ultrasound probe 5 to perform ultrasound transmissions in a first phase, e.g., an initial phase of 0 degrees and in a second phase, e.g., an initial phase of 180 degrees, different from the first phase. Accordingly, the receiver circuitry 11 receives, via the ultrasound probe 5, reception signals corresponding to the ultrasound transmissions of these two times.

Figure 7B:
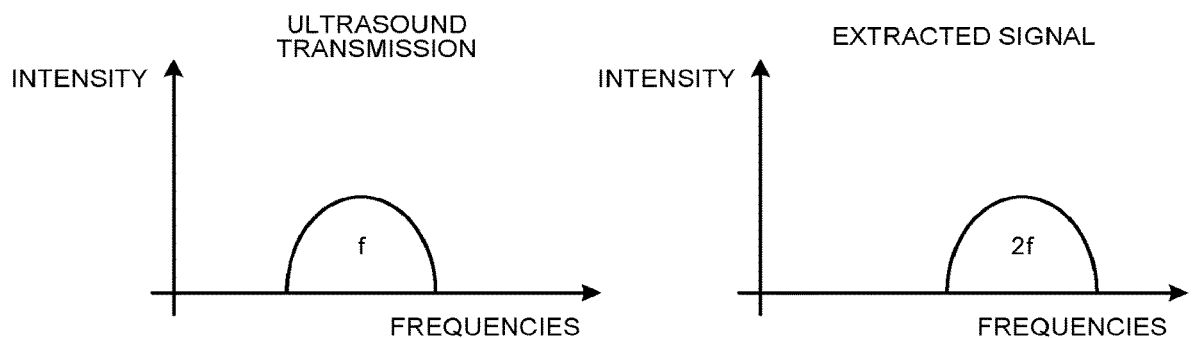

FIG. 7B illustrates an example in which the ultrasound transmissions which the transmitter circuitry 9 causes the ultrasound probe 5 to perform are ultrasound transmissions having a single frequency component f. In this situation, the transmitter circuitry 9 causes the ultrasound probe 5 to perform an ultrasound transmission which has the single frequency component f and of which the initial phase is 0 degrees and another ultrasound transmission which has the single frequency component f and of which the initial phase is 180 degrees. Via the ultrasound probe 5, the receiver circuitry 11 obtains the reception signals corresponding to these ultrasound transmissions as the first group of reception signals 20a and the third group of reception signals 20b. By employing the generating function 110z, the processing circuitry 110 generates a second image 2, by performing predetermined weighted addition on the first group of reception signals 20a and the third group of reception signals 20b and extracting a high-harmonic component signal corresponding to the frequency component at an overtone frequency 2f. For example, by employing the generating function 110z, the processing circuitry 110 generates the second image 2 represented by a non-linear component image, by extracting the high-harmonic component signal corresponding to the frequency component at the frequency 2f, by calculating the sum of the received reception signals.

However, possible embodiments are not limited to the example in which the ultrasound transmissions which the transmitter circuitry 9 causes the ultrasound probe 5 to perform are ultrasound transmissions having the single frequency component f. The ultrasound transmissions which the transmitter circuitry 9 causes the ultrasound probe 5 to perform may be ultrasound transmissions having a plurality of frequency components.

Figure 7C:
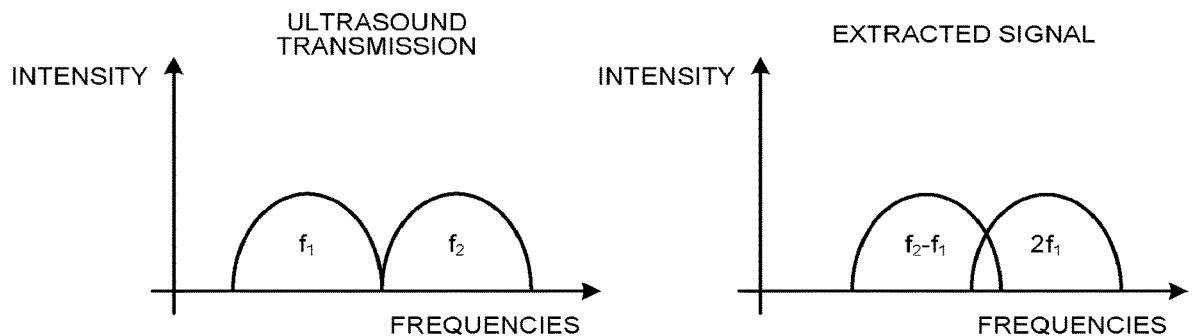

FIG. 7C illustrates an example in which the ultrasound transmissions which the transmitter circuitry 9 causes the ultrasound probe 5 to perform are ultrasound transmissions having a plurality of frequency components. In FIG. 7C, the letters $f_1$ and $f_2$ denote the plurality of frequency components. In the first ultrasound transmission and reception, the transmitter circuitry 9 causes the ultrasound probe 5 to perform an ultrasound transmission which have the plurality of frequency components $f_1$ and $f_2$ and of which the initial phase is 0 degrees. In the second ultrasound transmission and reception, the transmitter circuitry 9 causes the ultrasound probe 5 to perform an ultrasound transmission which have the plurality of frequency components $f_1$ and $f_2$ and of which the initial phase is 180 degrees.

Subsequently, the receiver circuitry 11 causes the ultrasound probe 5 to receive reception signals corresponding to these ultrasound transmissions and receptions. By employing the image performance function 110$z$, the processing circuitry 110 generates a second image 2 represented by a non-linear component image by extracting high-harmonic component signals corresponding to frequency components of $f_x-f_1$ and $2f_1$, for example, on the basis of the reception signals.

Further, the ultrasound transmissions which the transmitter circuitry 9 causes the ultrasound probe 5 to perform are not limited to ultrasound transmissions having two frequency components. For example, it is acceptable perform ultrasound transmissions twice, by performing ultrasound transmissions having three frequency components as a two-rate transmission. By performing addition or subtraction on the reception signals resulting from the ultrasound transmissions and receptions performed twice, the processing circuitry 110 is able to extract a harmonic component of an even-number order or an odd-number order. In addition, the processing circuitry 110 may extract a harmonic component of an odd-number order other than the fundamental component, by extracting the fundamental component with the use of a filter.

Further, possible embodiments are not limited to the example in which the ultrasound transmissions which the transmitter circuitry 9 causes the ultrasound probe 5 to perform are a two-rate transmission. The ultrasound transmissions may be a transmission of three or more rates. As examples of transmissions of three or more rates, FIGS. 8A, 8B, and 8C illustrate examples of three-rate transmissions.

Figure 8A:
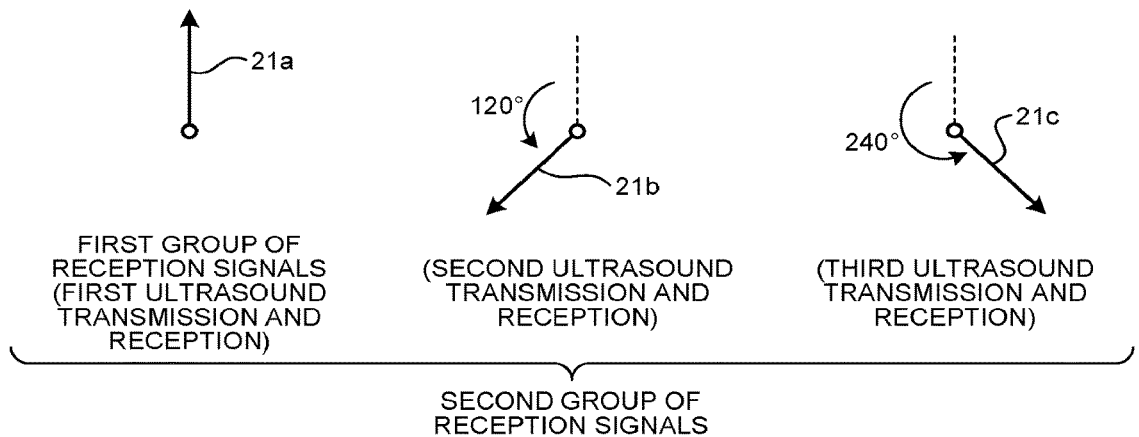
FIGS. 8A, 8B, and 8C present drawings for explaining other processes performed by the medical image processing apparatus according to the third modification example of the first embodiment.

In the present example, as illustrated in FIG. 8A, the transmitter circuitry 9 causes the ultrasound probe 5 to perform, for example, the first ultrasound transmission with an initial phase of 0 degrees; the second ultrasound transmission with an initial phase different from that of the first ultrasound transmission, e.g., with an initial phase of 120 degrees; and the third ultrasound transmission with an initial phase of 240 degrees. Subsequently, the receiver circuitry 11 causes the ultrasound probe 5 to receive reception signals corresponding to the ultrasound transmissions performed at the three times which the transmitter circuitry 9 causes the ultrasound probe 5 to perform. By employing the generating function 110$z$, the processing circuitry 110 generates a second image 2 represented by a non-linear component image by performing predetermined weighted addition on the received groups of reception signals 21$a$, 21$b$, and 21$c$ and extracting high-harmonic components.

Figure 8B:
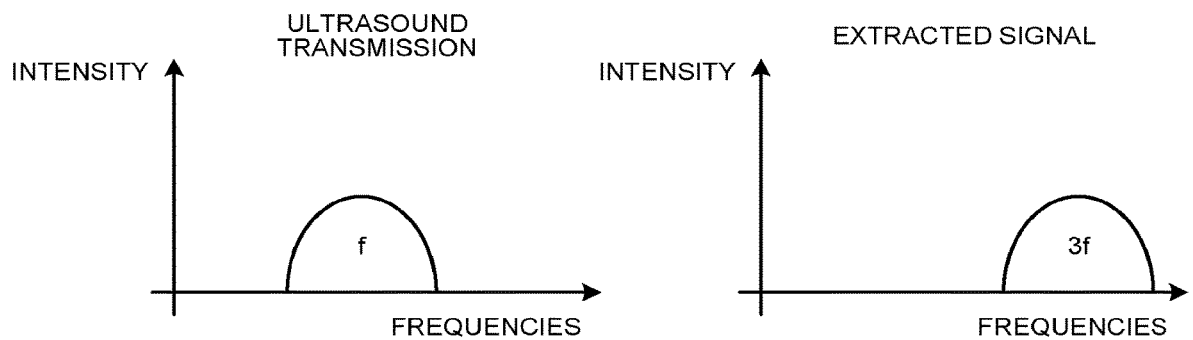

FIG. 8B illustrates an example in which the ultrasound transmissions which the transmitter circuitry 9 causes the ultrasound probe 5 to perform are ultrasound transmissions having the single frequency component f. In this situation, the transmitter circuitry 9 causes the ultrasound probe 5 to perform the ultrasound transmission three times while varying the phase. Subsequently, receiver circuitry 11 causes the ultrasound probe 5 to receive the reception signals respectively corresponding to the ultrasound transmissions. By employing the generating function 110$z$, the processing circuitry 110 extracts a signal having a high-harmonic component corresponding to a frequency component at the frequency $3f$, by performing a predetermined adding process on the groups of reception signals 21$a$, 21$b$, and 21$c$.

Figure 8C:
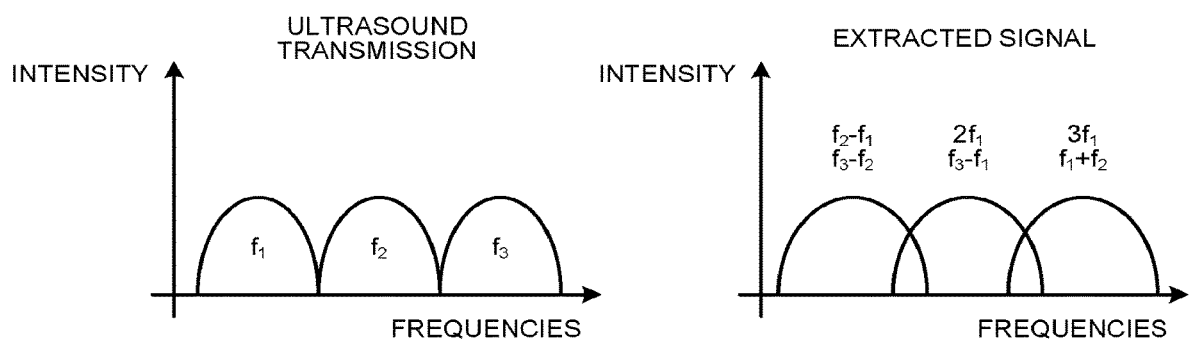

As another example, FIG. 8C illustrates an example in which the ultrasound transmissions which the transmitter circuitry 9 causes the ultrasound probe 5 to perform are ultrasound transmissions having a plurality of frequency components. For example, the transmitter circuitry 9 causes the ultrasound probe 5 to transmit an ultrasound wave having three frequency components $f_1$, $f_2$, and $f_3$ at two rates while inverting the phase. Subsequently, the receiver circuitry 11 causes the ultrasound probe 5 to receive the reception signals respectively corresponding to the ultrasound transmissions. By employing the generating function 110$z$, the processing circuitry 110 extracts a signal having high-harmonic components corresponding to the frequency components of $f_2-f_1$, $f_3-f_2$, $2f_2$, $f_3$ $f_1$, $3f_2$, and $f_1+f_2$, for example, by performing an adding process, a subtracting process, a filtering process, and/or the like on the received reception signals.

Other Modification Examples of First Embodiment

In the embodiment, the example was explained in which, at step S110 in FIG. 3, by employing the training data generating function 110$c$, the processing circuitry 110 generates the first image 1 as the first data set, and at step S120, further generates the second image 2 as the second data set, so as to perform the learning process by using the generated data sets; however, possible embodiments are not limited to this example. For instance, the first data set does not necessarily have to be an image and may be a group of reception signals (ch signals) before a beam forming process is performed, for example, or may be a group of reception signals after a beam forming process is performed. Similarly, the second data set does not necessarily have to be an image and may be a group of reception signals before a beam forming process is performed, for example, or may be after reception signals after a beam forming process is performed. In other words, the first data set, the second data set, and the output data set do not each necessarily have to include an image data set. For example, the first data set, the second data set, and the output data set may each include a plurality of channel data sets used for generating a scanning line data set. For example, in an embodiment, a trained model may be generated through a learning process, by using a plurality of first channel data sets as an input; and using a plurality of third channel data sets obtained by combining, for each channel, the plurality of first channel data sets with a plurality of second channel data sets as an output. In the present example, the plurality of first channel data sets and the plurality of second channel data sets correspond, for example, to ultrasound waves successively transmitted and received as many times as the second number for the same scanning line. In this situation, the plurality of first channel data sets and the plurality of second channel data sets are, typically, obtained by ultrasound transmissions and receptions to and from a site different from the heart. In contrast, the plurality of third channel data sets are obtained by ultrasound transmissions and receptions to and from the heart.

For example, by employing the training data generating function 110$c$, the processing circuitry 110 generates a trained model by: generating a group of reception signals prior to a beam forming process as a first data set at step S110; generating a group of reception signals prior to a beam forming process as a second data set at step S120; and performing a learning process by using the first data set and the second data set as a set made up of input data and output data, respectively, at step S130.

In yet another example, by employing the training data generating function 110c, the processing circuitry 110 may generate a trained model by: generating a group of reception signals after a beam forming process as a first data set at step S110; generating a group of reception signals after a beam forming process as a second data set at step S120; and performing a learning process by using the first data set and the second data set as a set made up of input data and output data, respectively, at step S130.

Examples in which the group of reception signals prior to a beam forming process and the group of reception signals after a beam forming process are used as the first data set and the second data set will be explained in details in a second embodiment and a third embodiment below.

Further, in the embodiments, the input data and the output data used by the trained model, i.e., the first data set and the second data set, do not necessarily have to be data sets related to mutually the same processing stages and may be data sets related to mutually-different processing stages. For example, the group of reception signals after a beam forming process may be used as input data (the first data set) for a trained model, while an image is used as output data (the second data set) for the trained model. In another example, for instance, the group of reception signals prior to a beam forming process may be used as the first data set, while the group of reception signals after a beam forming process is performed is used as the second data set.

Further, similarly in the second and other embodiments, the first data set that is the data set input to the trained model and the second data set that is the data set output from the trained model described above may be data in any of various forms and formats as explained above. In the embodiments described below, the first data set, the second data set, and the like may also similarly be carried out in modification examples related to the data in the various forms and formats described above.

Further, although the example was explained in which the transmission parameter varied by the transmitter circuitry 9 for each scanning line is the phase of the transmitted ultrasound wave, possible embodiments are not limited to this example. For instance, an embodiment may be applied to a space compound, i.e., the parameter varied by the transmitter circuitry 9 for each scanning line is the direction of the beam. In other words, when generating the second image 2 represented by a non-linear component image, the transmission parameter transmitter circuitry 9 performs a plurality of ultrasound transmissions and receptions, while varying the direction of the beam.

Further, in the embodiment, the example was explained in which the transmitter circuitry 9 causes the ultrasound probe 5 to perform the ultrasound transmission multiple times for each scanning line, so that the processing circuitry 110 generates both the first image 1 and the second image 2 from the data obtained in the ultrasound transmission performed multiple times, by employing the generating function 110z; however, possible embodiments are not limited to this example. The first image 1 does not necessarily have to be generated from the data of the scan from which the second image 2 was generated. The first image 1 and the second image 2 may be generated on the basis of mutually-different scans.

Further, another arrangement is also acceptable in which a user provides feedback regarding an output image generated by the processing circuitry 110 with an application of the trained model, so that the processing circuitry 110 updates an internal algorithm of the trained model on the basis of the feedback provided by the user, by employing the learning function 110d. In other words, by employing the learning function 110d, the processing circuitry 110 may perform an autolearning process, by continuing to update the trained model on the basis of the feedback from the user.

Second Embodiment

In the first embodiment, the example was explained in which, by employing the learning function 110d, the processing circuitry 110 generates the trained model through the learning process, by using the first image 1 and the second image 2 as the input and the output, respectively; however, possible embodiments are not limited to performing a learning process using images. It is also acceptable to perform a learning process by using intermediate data before generating images, e.g., RF signals resulting from a Delay and Sum process or IQ signals resulting from a quadrature detection process.

Figure 10:
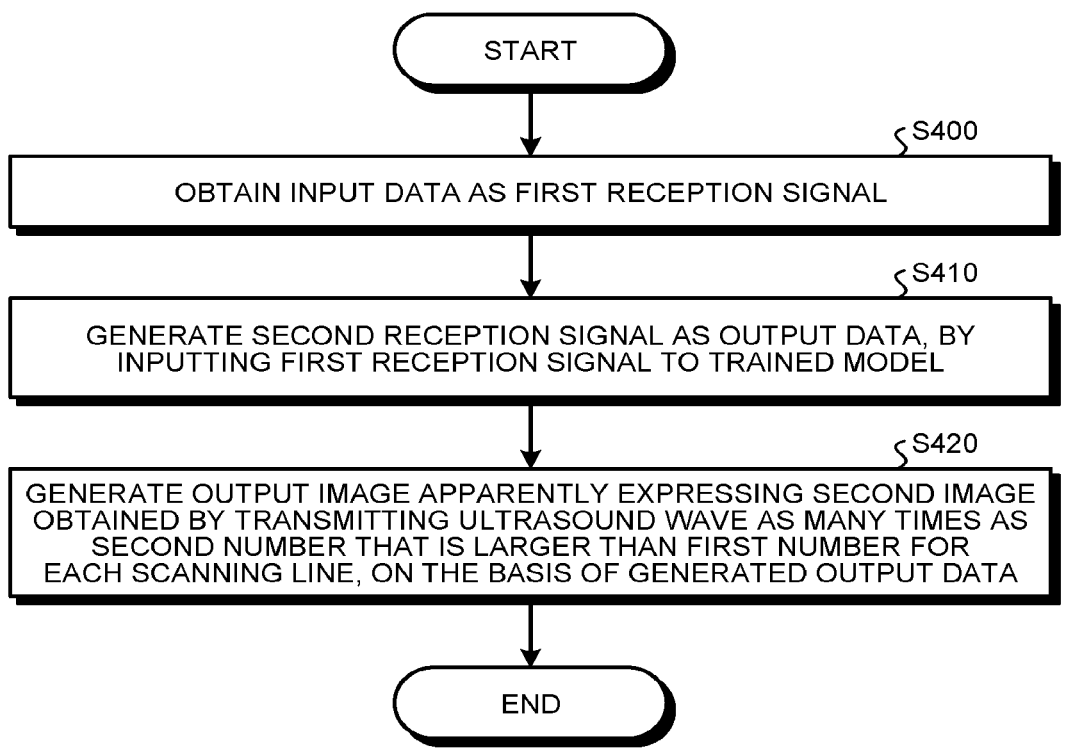
FIG. 10 is a flowchart for explaining a flow in a process of implementing a trained model performed by the medical image processing apparatus according to the second embodiment.

This configuration will be explained, with reference to FIGS. 9 and 10. FIG. 9 is a flowchart for explaining a flow in a learning process performed by a medical image processing apparatus according to the second embodiment.

To begin with, a flow in a process at the trained model generating stage will be explained, with reference to FIG. 9.

At first, the transmitter circuitry 9 causes the ultrasound probe 5 to transmit an ultrasound wave as many times as the second number that is larger than the first number, while varying the transmission parameter for each scanning line. For example, the transmitter circuitry 9 causes the ultrasound probe 5 to transmit the ultrasound wave twice for each scanning line, while varying the phase of the transmitted ultrasound wave for each scanning line.

Subsequently, the receiver circuitry 11 causes the ultrasound probe 5 to receive the reception signals corresponding to the ultrasound waves caused by the transmitter circuitry 9 to be transmitted, as a second group of reception signals including the first group of reception signals 20a.

At step S300, by employing the training data generating function 110c, the processing circuitry 110 obtains, on the basis of the first group of reception signals 20a, first data represented by a group of signal data such as RF signals resulting from a Delay and Sum process or IQ signals, from the receiver circuitry 11, as a first reception signal, by employing the interface function 110x or the like. The first data is, for example, data corresponding to the two axes in the beam direction and in the depth direction and is intermediate data used for generating the first image 1. The Delay and Sum process is, for example, executed by the processing circuitry 110 as a software process. Alternatively, the output data (the group of reception signals) may be input to the receiver circuitry 11 so that the receiver circuitry 11 executes the Delay and Sum process. As explained herein, in the second embodiment, the first reception signal is the reception signal after the beam forming process is performed.

Subsequently, at step S310, by employing the training data generating function 110c, the processing circuitry 110 obtains, on the basis of the second group of reception signals, second data represented by signal data of RF signals resulting from the Delay and Sum process or IQ signals, from the receiver circuitry 11 as a second reception signal, by employing the interface function 110x or the like. The second data is, for example, two-dimensional data corresponding to the two axes in the beam direction and in the depth direction and is obtained by combining, for each of the corresponding positions, the group of reception signals included in the second group of reception signals. Further, the second data is, for example, intermediate data used for generating the second image 2. As explained herein, in the second embodiment, the second reception signal is the reception signal after a beam forming process is performed.

Subsequently, at step S320, by employing the learning function 110d, the processing circuitry 110 generates a trained model by performing a learning process while using a neural network for example, by using the first data and the second data as a set made up of input data and output data, respectively. On the basis of the first reception signal represented by the group of signal data resulting from the Delay and Sum process and obtained by transmitting and receiving an ultrasound wave as many times as the first number, for a scanning line, the trained model generates, as an output data set, an output signal apparently expressing the second reception signal represented by a group of signal data resulting from a Delay and Sum process and obtained by transmitting and receiving an ultrasound wave as many times as the second number that is larger than the first number for the scanning line.

The processes at steps S300 through S320 are the same as those at steps S110 through S130, except that what is learned is the intermediate data corresponding to each channel, for example; however, in the second embodiment, because the learning process is performed by using the group of data obtained in the process at an earlier stage than in the first embodiment, the image quality is expected to be further enhanced.

Next, a process at the stage of implementing the trained model will be explained with reference to FIG. 10. FIG. 10 is a flowchart for explaining a flow in the process of implementing the trained model performed by the medical image processing apparatus according to the second embodiment.

At step S400, by employing the interface function 110x, the processing circuitry 110 obtains, from the receiver circuitry 11, the memory 132, or the like, input data represented by intermediate data before generating an input image obtained by transmitting and receiving an ultrasound wave as many times as the first number for each scanning line and represented by a group of signal data of RF signals resulting from a Delay and Sum process or IQ signals, as a first reception signal.

After that, at step S410, by employing the generating function 110z, the processing circuitry 110 generates a second reception signal as output data corresponding to the second data, on the basis of the input data obtained at step S400 and the trained model generated by the processing circuitry 110 by employing the learning function 110d. In other words, by employing a processing unit (not illustrated), the processing circuitry 110 generates the output signal as the second reception signal, by inputting the input reception signal obtained by transmitting and receiving the ultrasound wave as many times as the first number for the scanning line as the first reception signal, to the trained model generated at step S320.

Subsequently, at step S420, by employing the generating function 110z, the processing circuitry 110 generates an output image apparently expressing the second image obtained by transmitting an ultrasound wave as many times as the second number that is larger than the first number for each scanning line, on the basis of the output data generated at step S410. In other words, by employing the generating function 110z, the processing circuitry 110 generates the image on the basis of the output signal generated at step S410.

Similarly to the first embodiment, by employing the generating function 110z, the processing circuitry 110 may further obtain a combined image by combining an image obtained from the input data acquired at step S400 with the image generated at step S420, at a ratio corresponding to positions in the axial direction. The combining process in the situation where a plurality of trained models are generated is also the same as that in the first embodiment. Further, possible embodiments are not limited to using the groups of signal data resulting from the Delay and Sum process as the input and the output. By employing the learning function 110d, the processing circuitry 110 may perform a learning process by using groups of signal data before and after any of other types of processes or by using signal data immediately after being received.

As explained above, in the second embodiment, the processing circuitry 110 performs the learning process by using the groups of signal data instead of the images. It is therefore possible to further enhance the image quality.

Third Embodiment

In the second embodiment, as an example of a learning process using a data format other than images, the example was explained in which the processing circuitry 110 performs the learning process by employing the learning function 110d, by using the groups of signals after a beam forming process, e.g., the RF signals resulting from the Delay and Sum process or the IQ signals resulting from the quadrature detecting process, as the first data set and the second data set. In the third embodiment, as another example of a learning process using a data format other than images, an example will be explained in which a learning process is performed by using groups of signals from a process at an even earlier stage, e.g., pieces of data corresponding to different channels prior to a beam forming process using a Delay and Sum process, as the first data set and the second data set.

In the third embodiment, because the learning process is performed by using the data from the process at an even earlier stage than in the second embodiment, it is possible to eliminate effects of noise and the like occurring at the earlier stage. The image quality is therefore expected to be enhanced.

This configuration will be explained, with reference to FIGS. 9 and 10 again. The third embodiment is different from the second embodiment for the type of data used as the first data set and the second data set. The other processes are the same as those in the second embodiment. In the following sections, duplicate explanations of the processes that are the same as those in the second embodiment will be omitted.

To begin with, a flow in a process at the stage of generating a trained model will be explained, with reference to FIG. 9.

Similarly to the second embodiment, at first, the transmitter circuitry 9 causes the ultrasound probe 5 to transmit an ultrasound wave as many times as the second number that is larger than the first number, while varying the transmission parameter for each scanning line. For example, the transmitter circuitry 9 causes the ultrasound probe 5 to transmit an ultrasound wave twice for each scanning line, while varying the phase of the transmitted ultrasound wave for each scanning line.

Subsequently, the receiver circuitry 11 causes the ultrasound probe 5 to receive the reception signals corresponding to the ultrasound waves caused by the transmitter circuitry 9 to be transmitted, as a second group of reception signals including the first group of reception signals 20a.

At step S300, by employing the training data generating function 110c, the processing circuitry 110 obtains, on the basis of the first group of reception signals 20a, first data represented by the data corresponding to each channel prior to a Delay and Sum process and represented by the intermediate data before generating the first image 1, as a first reception signal, by employing the interface function 110x or the like. The first data is, for example, three-dimensional volume data corresponding to the channel direction, the beam direction, and the depth direction. As explained herein, in the third embodiment, the first reception signal is the reception signal prior to the beam forming process.

Subsequently, at step S310, by employing the training data generating function 110c, the processing circuitry 110 obtains, on the basis of the second group of reception signals, second data represented by the data corresponding to each channel prior to the Delay and Sum process and represented by the intermediate data before generating the second image 2, from the receiver circuitry 11 as a second reception signal, by employing the interface function 110x or the like. As explained herein, in the third embodiment, the second reception signal is the reception signal prior to the beam forming process.

Subsequently, at step S320, by employing the learning function 110d, the processing circuitry 110 generates a trained model through a learning process using a neural network, for example, by using the first data and the second data as a set made up of input data and output data, respectively. On the basis of the first reception signal represented by the data used for generating an ultrasound image obtained by transmitting and receiving an ultrasound wave as many times as the first number, for each scanning line and represented by the data corresponding to each channel prior to the Delay and Sum process, the trained model generates, as an output data set, an output signal apparently expressing a second reception signal represented by data used for generating an ultrasound image obtained by transmitting and receiving an ultrasound wave as many times as the second number that is larger than the first number for the scanning line and represented by data corresponding to each channel prior to the Delay and Sum process.

Next, a process performed at the stage of implementing the trained model will be explained, with reference to FIG. 10 again.

At step S400, by employing the interface function 110x, the processing circuitry 110 obtains, from the receiver circuitry 11, the memory 132, or the like, first data represented by intermediate data before generating an input image obtained by transmitting and receiving an ultrasound wave as many times as the first number for each scanning line and represented by data corresponding to each channel prior to the Delay and Sum process, as a first reception signal.

Subsequently, at step S410, by employing a processing unit (not illustrated), the processing circuitry 110 generates a second reception signal as output data, by inputting the first reception signal to the trained model generated at step S320.

After that, because the generated data is merely the intermediate data at the stage when step S410 has finished, a process including the Delay and Sum process, for example, is performed to convert the pieces of data into an image format. At step S420, by employing the generating function 110z, the processing circuitry 110 generates an output image apparently expressing the second image obtained by transmitting an ultrasound wave as many times as the second number that is larger than the first number for each scanning line, on the basis of the output data generated at step S410. In other words, by employing the generating function 110z, the processing circuitry 110 generates the image on the basis of the output signal generated at step S410. In this situation, the Delay and Sum process is, for example, executed by the processing circuitry 110 as a software process. Alternatively, the output data (the group of reception signals) generated at the stage when step S410 has finished may be input to the receiver circuitry 11 so that the receiver circuitry 11 executes the Delay and Sum process.

Similarly to the second embodiment, by employing the generating function 110z, the processing circuitry 110 may further obtain a combined image, by combining an image obtained from the input data acquired at step S400 with the image generated at step S420, at a ratio corresponding to positions in the axial direction.

As explained above, in the third embodiment, the processing circuitry 110 performs the learning process by using the data at the earlier stage than in the second embodiment. As a result, it is possible to further enhance the image quality.

Fourth Embodiment

In the first embodiment, the example was explained in which, by employing the learning function 110d, the processing circuitry 110 performs the learning process by using the linear component image as an input and using the non-linear component image as an output. In other words, in the above example, the processing circuitry 110 performs the learning process by employing the learning function 110d, by using the image having relatively low image quality as the input and using the image having high image quality as the output, so as to calculate the image having high image quality on the basis of the image having low image quality; however, possible embodiments are not limited to this example. In a fourth embodiment, by employing the learning function 110d, the processing circuitry 110 performs a learning process by using a difference image between an image having high image quality and an image having low image quality as an output. As a result, the processing circuitry 110 is able to identify a location where the image quality is degraded or where an artifact is occurring.

Figure 11:
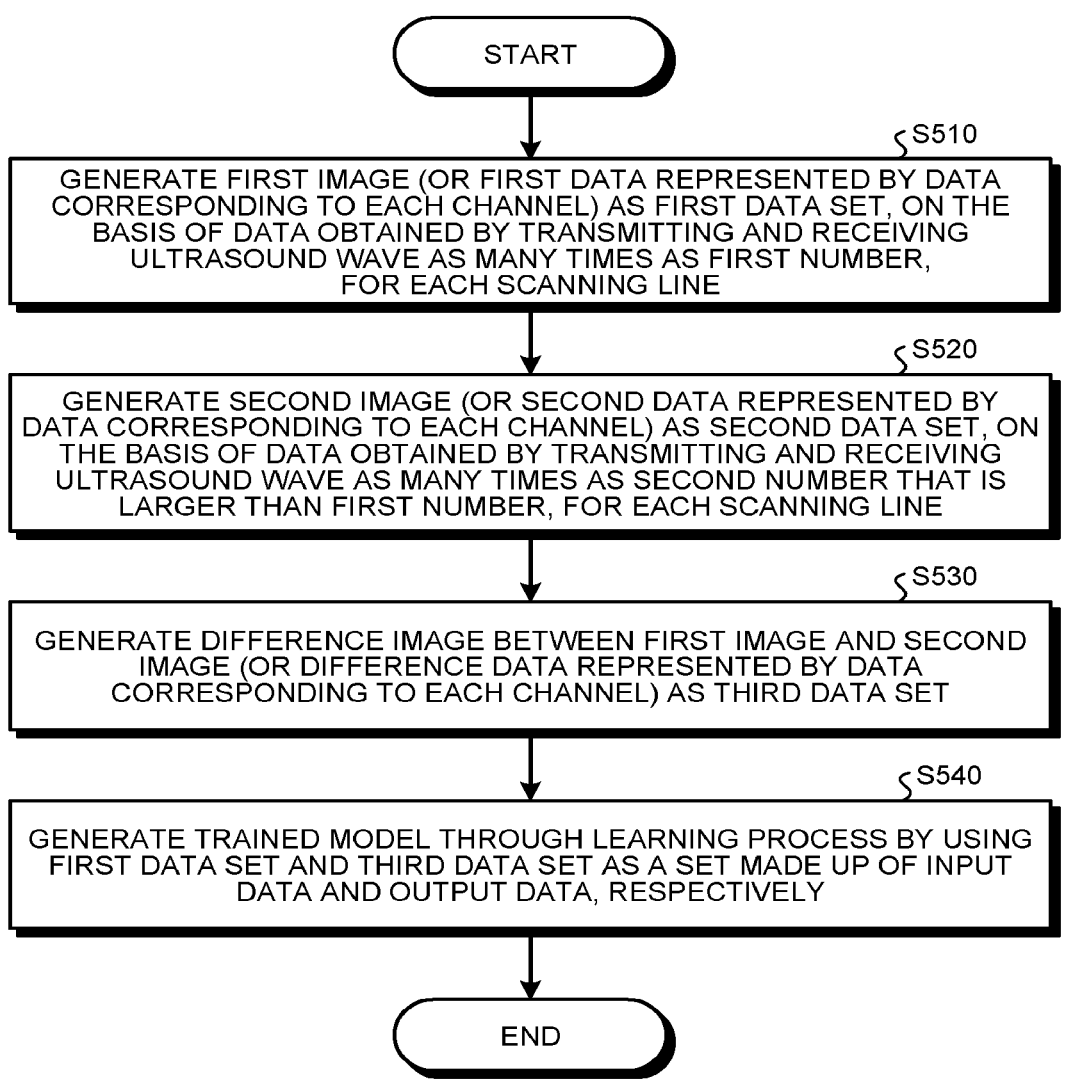
FIG. 11 is a flowchart for explaining a flow in a process of implementing a trained model performed by a medical image processing apparatus according to a fourth embodiment.

This configuration will be explained with reference to FIGS. 11 and 12. FIG. 11 is a flowchart for explaining a flow in a process of implementing a trained model performed by a medical image processing apparatus according to the fourth embodiment.

To begin with, a flow in a process at the stage of generating the trained model will be explained, with reference to FIG. 11.

At first, the transmitter circuitry 9 causes the ultrasound probe 5 to transmit an ultrasound wave as many times as the second number that is larger than the first number while varying the transmission parameter for each scanning line. For example, the transmitter circuitry 9 causes the ultrasound probe 5 to transmit an ultrasound wave twice for each scanning line, while varying the phase of the transmitted ultrasound wave for each scanning line.

Subsequently, the receiver circuitry 11 causes the ultrasound probe 5 to receive the reception signals corresponding to the ultrasound waves caused by the transmitter circuitry 9 to be transmitted, as a second group of reception signals including the first group of reception signals 20a.

At step S510, by employing the training data generating function 110c, the processing circuitry 110 generates, when performing the learning process by using images, a first image 1 as a first data set, on the basis of the first group of reception signals 20a represented by the data obtained by transmitting and receiving an ultrasound wave as many times as the first number for each scanning line. In another example, by employing the training data generating function 110c, the processing circuitry 110 generates, as a first data set, a group of signal data of RF signals resulting from the Delay and Sum process or IQ signals.

In yet another example, by employing the training data generating function 110c, the processing circuitry 110 generates, when performing the learning process by using data corresponding to each channel, first data represented by the data corresponding to each channel, as a first data set, on the basis of the first group of reception signals 20a.

Further, at step S520, by employing the training data generating function 110c, the processing circuitry 110 generates, when performing the learning process by using images, a second image 2 as a second data set, on the basis of a second group of reception signals represented by data obtained by transmitting and receiving an ultrasound wave as many times as the second number that is larger than the first number, for each scanning line.

Further, in another example, by employing the training data generating function 110c, the processing circuitry 110 generates, as a second data set, a group of signal data of RF signals resulting from a Delay and Sum process or IQ signals. In yet another example, by employing the training data generating function 110c, the processing circuitry 110 generates, when performing the learning process by using data corresponding to each channel, second data represented by the data corresponding to each channel, on the basis of the second group of reception signals. The processes at steps S510 and S520 are the same as the processes at steps S110 and S120 or the processes at steps S300 and S310.

After that, at step S530, by employing the training data generating function 110c, the processing circuitry 110 generates a difference image between the first image and the second image generated at step S510, as a third data set, or alternatively, generates difference data between the first data and the second data represented by the pieces of data corresponding to the different channels, for example.

Subsequently, at step S540, by employing the learning function 110d, the processing circuitry 110 generates a trained model through a learning process by using the first data set and the third data set as a set made up of input data and output data, respectively. For example, by employing the learning function 110d, the processing circuitry 110 generates the trained model through the learning process by using the first image and the difference image as the set made up of input data and output data, respectively, or alternatively, generates the trained model through the learning process by using the first data and the difference data as the set made up of input data and output data, respectively. On the basis of the first image represented by the first data set obtained by transmitting and receiving an ultrasound wave as many times as the first number for each scanning line, the trained model is configured to apparently generate, as a third data set serving as an output data set, an output image apparently expressing a difference image between the first image and the second image represented by the second data set obtained by transmitting and receiving an ultrasound wave as many times as the second number that is larger than the first number for each scanning line, i.e., expressing the difference between the second data set and the first data set.

In this situation, the difference image represents the difference between the first image considered to have relatively low image quality and the second image considered to have relatively high image quality. In the difference image, a location having larger pixel values is considered to be a region where the image quality is degraded due to an artifact or the like, for example. Accordingly, by performing the learning process by using the difference image as the output data while employing the learning function 110d, the processing circuitry 110 is able to identify the region considered to have an image quality degradation due to the artifact or the like and is able to perform image processing processes by using the identified region.

Next, a process at the stage of implementing the trained model will be explained, with reference to FIG. 12. FIG. 12 is a flowchart for explaining a flow in another process of implementing the trained model performed by the medical image processing apparatus according to the fourth embodiment.

At step S600, by employing the interface function 110x, the processing circuitry 110 obtains, from the receiver circuitry 11, the memory 132, or the like, an input image (or input data corresponding to each channel) obtained by transmitting and receiving an ultrasound wave as many times as the first number for each scanning line, as a first data set.

Subsequently, at step S610, by employing the generating function 110z, the processing circuitry 110 generates an output image apparently expressing the difference image i.e., expressing the difference between the first data set and the second data set, as a third data set serving as an output data set, by inputting the input image (or the input data corresponding to each channel) obtained at step S600 by transmitting and receiving an ultrasound wave as many times as the first number for each scanning line, to the trained model generated by the processing circuitry 110 at step S540 while employing the learning function 110d.

After that, at step S620, by employing an identifying function (not illustrated), the processing circuitry 110 identifies a low image-quality location on the basis of the output image generated at step S610. In one example, by employing the identifying function, the processing circuitry 110 identifies a location where the absolute values of the values in the output image generated at step S610 exceed a reference value, as the low image-quality location.

Subsequently, at step S630, by employing the generating function 110z, the processing circuitry 110 performs an image quality enhancing process (a noise reduction process) on the low image-quality location identified at step S620 within the input image (or an image structured from the input data corresponding to each channel) obtained at step S600. More specifically, the processing circuitry 110 performs a process of replacing the pixel values of the pixels in the low image-quality location within the input image, with an average value of surrounding pixels, or the like.

After that, at step S640, by employing the generating function 110z, the processing circuitry 110 generates the input image on which the image quality enhancing process was performed at step S630, as a pseudo-second image represented by an image apparently expressing the second image and serving as a second data set.

As explained herein, in the third embodiment, it is possible to enhance the image quality by identifying the low image-quality location through the learning process and performing the image quality enhancing process.

In the above embodiments, the example was explained in which the ultrasound diagnosis apparatus main body 10 includes the medical image processing apparatus 100, whereas the processing circuitry 110 included in the medical image processing apparatus 100 performs both the generation and the application of the trained model by employing the training data generating function 110c, the learning function 110d, the generating function 110z, and the like; however, the present disclosure is not limited to this example.

For instance, the processing circuitry 110 of the medical image processing apparatus 100 included in the ultrasound diagnosis apparatus main body 10 does not necessarily have to be capable of executing the training data generating function 110c and the learning function 110d, while being capable of executing the generating function 110z. Conversely, for example, the processing circuitry 110 of the medical image processing apparatus 100 included in the ultrasound diagnosis apparatus main body 10 does not necessarily have to be capable of executing the training data generating function 110c and the learning function 110d, while being capable of executing the training data generating function 110c and the learning function 110d and being capable of executing the generating function 110z.

For example, the generating function 110z may be executed by a processing circuitry (not illustrated) provided in a first medical image processing apparatus (not illustrated) different from the medical image processing apparatus 100.

It is ideal when the processing circuitry 110 of the medical image processing apparatus 100 executes the generating function 110z to obtain an output image having high image quality in a real-time manner; however, depending on capabilities of the processing circuitry 110, it may be impossible, in some situations, to obtain an output image in a real-time manner due to an increase in the processing load. Accordingly, by separating the generating function 110z from the functions of the processing circuitry 110, the ultrasound diagnosis apparatus main body 10 required to have excellent real-time property is able to cause a display to display an input image in a real-time manner by employing the controlling function 110y and is able to generate an output image having high image quality at the time of analyses which do not require excellent real-time property. Further, for example, the generating function 110z may be applied only to the times when a freeze operation or a saving operation is received or only to the data sets acquired within a predetermined time period before and after such times.

For example, the learning process performed by the training data generating function 110c and a learning function 110d may be executed by a processing circuitry (not illustrated) provided in the first medical image processing apparatus (not illustrated) different from the medical image processing apparatus 100 included in the ultrasound diagnosis apparatus main body 10.

As explained above, by using the medical image processing apparatus according to at least one aspect of the embodiments, it is possible to efficiently obtain the information useful for diagnosing processes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured:
to generate an output data set apparently expressing a second data set obtained by transmitting and receiving an ultrasound wave, for each scanning line, as many times as a second number that is larger than a first number, by inputting a first data set to a trained model that generates the output data set on a basis of the first data set obtained by transmitting and receiving an ultrasound wave, for each scanning line, as many times as the first number.

2. The medical image processing apparatus according to claim 1, wherein the first data set and the output data set each include an image data set.

3. The medical image processing apparatus according to claim 1, wherein the first data set and the output data set each include a plurality of channel data sets for generating a scanning line data set.

4. The medical image processing apparatus according to claim 1, wherein the output data set apparently expresses the second data set obtained by transmitting an ultrasound wave as many times as the second number while varying a transmission parameter for each scanning line.

5. The medical image processing apparatus according to claim 4, wherein the transmission parameter includes a phase of the transmitted ultrasound wave.

6. The medical image processing apparatus according to claim 2, wherein
the trained model is generated through a learning process, by using a linear component image data set based on a plurality of first scanning line data sets as an input and using a non-linear component image data set based on a plurality of second scanning line data set groups including the plurality of first scanning line data sets as an output, and
the plurality of second scanning line data sets correspond to ultrasound waves successively transmitted and received as many times as the second number, for each scanning line.

7. The medical image processing apparatus according to claim 6, wherein the non-linear component image data set is generated by combining, for each scanning line, the plurality of second scanning line data sets.

8. The medical image processing apparatus according to claim 7, wherein the trained model is generated through a learning process, by using another linear component image data set based on a plurality of third scanning line data sets that are included in the plurality of second scanning line data sets and are different from the plurality of first scanning line data sets as an input and using the non-linear component image data set as an output.

9. The medical image processing apparatus according to claim 8, wherein
the plurality of first scanning line data sets correspond to an ultrasound wave transmitted in a first phase, and
the plurality of third scanning line data sets correspond to an ultrasound wave transmitted in a second phase different from the first phase.

10. The medical image processing apparatus according to claim 3, wherein
the trained model is generated through a learning process, by using a plurality of first channel data sets as an input and using a plurality of third channel data sets obtained by combining, for each channel, the plurality of first channel data sets with a plurality of second channel data sets as an output, and the plurality of first channel data sets and the plurality of second channel data sets correspond to ultrasound waves successively transmitted and received as many times as the second number, for a same scanning line.

11. The medical image processing apparatus according to claim 7, wherein the non-linear component image data set is an image data set based on at least one selected from among a harmonic component of a second order or higher, a difference tone component, and a sum tone component included in each of the plurality of second scanning line data sets.

12. The medical image processing apparatus according to claim 2, wherein
the trained model is generated through a learning process, by using a first non-linear component image data set based on a plurality of first scanning line data sets as an input and using a second non-linear component image data set based on a plurality of second scanning line data sets including the plurality of first scanning line data sets as an output, and
the plurality of second scanning line data sets correspond to ultrasound waves successively transmitted and received as many times as the second number, for each scanning line.

13. The medical image processing apparatus according to claim 12, wherein
the first non-linear component image data set is generated by applying a frequency filter to the plurality of first scanning line data sets, and
the second non-linear component image data set is generated by combining, for each scanning line, the plurality of second scanning line data sets.

14. The medical image processing apparatus according to claim 1, wherein the first number is 1, whereas the second number is 2.

15. The medical image processing apparatus according to claim 1, wherein the trained model generates the output data set having a higher lateral resolution and a higher axial resolution than the first data set, on the basis of the first data set.

16. The medical image processing apparatus according to claim 6, wherein
the image data set renders a heart, and
the linear component image data set and the non-linear component image data set do not render the heart.

17. The medical image processing apparatus according to claim 10, wherein
the plurality of third channel data sets are obtained by transmitting and receiving an ultrasound wave to and from a heart, and
the plurality of first channel data sets and the plurality of second channel data sets are obtained by transmitting and receiving an ultrasound wave to and from a site different from the heart.

18. The medical image processing apparatus according to claim 1, wherein the processing circuitry generates a combined data set by combining the first data set with the output data set, at a ratio corresponding to positions in a axial direction.

19. A medical image processing apparatus comprising processing circuitry configured:
to generate an output data set apparently expressing a second scanning line data set obtained by transmitting and receiving an ultrasound wave as many times as a second number that is larger than a first number, for a scanning line, by inputting a first scanning line data set to a trained model that generates the output data set on a basis of the first scanning line data set obtained by transmitting and receiving an ultrasound wave as many times as the first number for the scanning line; and
to generate an image on a basis of the output data set.

20. A medical image processing apparatus comprising processing circuitry configured:
to generate an output data set expressing a difference between a second data set and a first data set, by inputting the first data set to a trained model that generates the output data set on a basis of the first data set obtained by transmitting and receiving an ultrasound wave as many times as a first number for each scanning line, the second data set being obtained by transmitting and receiving an ultrasound wave as many times as a second number that is larger than the first number for each scanning line.

21. An ultrasound diagnosis apparatus comprising the medical image processing apparatus according to claim 1.

22. A trained model generating method comprising:
a step of obtaining one selected from between a linear component image data set and a first non-linear component image data set that is based on a plurality of first scanning line data sets and a second non-linear component image data set based on a plurality of second scanning line data sets including the plurality of first scanning line data sets; and
a step of generating a trained model by using the one selected from between the linear component image data set and the first non-linear component image data set as an input-side training-purpose data set and using the second non-linear component image data set as an output-side training-purpose data set.

23. The trained model generating method according to claim 22, wherein upon receipt of an input of a first image data set obtained by transmitting and receiving an ultrasound wave as many times as a first number, for each scanning line, the trained model generates an output image data set apparently expressing a second image data set obtained by transmitting and receiving an ultrasound wave as many times as a second number that is larger than the first number, for each scanning line.

* * * * *